(12) United States Patent
Parks

(10) Patent No.: US 8,306,604 B2
(45) Date of Patent: Nov. 6, 2012

(54) METHOD OF MEASURING AND DISPLAYING THE POSITION OF RADIOGRAPHICALLY CONTRASTED MATERIAL WITHIN LUMINAL BODY ORGANS

(75) Inventor: Thomas R. Parks, Hermosa Beach, CA (US)

(73) Assignee: Sierra Scientific Instruments, LLC, Los Angeles, CA (US)

( * ) Notice: Subject to any disclaimer, the term of this patent is extended or adjusted under 35 U.S.C. 154(b) by 1062 days.

(21) Appl. No.: 12/249,805

(22) Filed: Oct. 10, 2008

(65) Prior Publication Data

US 2009/0257554 A1    Oct. 15, 2009

Related U.S. Application Data

(60) Provisional application No. 60/998,526, filed on Oct. 11, 2007.

(51) Int. Cl.
    *A61B 5/05*      (2006.01)
(52) U.S. Cl. .................. 600/420; 382/132; 600/407
(58) Field of Classification Search .......... 600/407–435, 600/437–465; 382/128–132
See application file for complete search history.

(56) References Cited

U.S. PATENT DOCUMENTS

| | | | |
|---|---|---|---|
| 3,608,061 A | | 9/1971 | McNally |
| 4,850,351 A | | 7/1989 | Herman et al. |
| 5,024,240 A | * | 6/1991 | McConnel .................. 600/593 |
| 5,045,071 A | * | 9/1991 | McCormick et al. ......... 604/529 |
| 5,209,730 A | * | 5/1993 | Sullivan .................... 604/103.1 |
| 5,239,982 A | * | 8/1993 | Trauthen .................... 600/117 |
| 5,263,928 A | * | 11/1993 | Trauthen et al. ............ 604/509 |
| 5,364,354 A | * | 11/1994 | Walker et al. ............ 604/103.1 |
| 5,419,324 A | | 5/1995 | Dillow |
| 5,571,093 A | | 11/1996 | Cruz et al. |
| 5,606,981 A | | 3/1997 | Tartacower et al. |

(Continued)

FOREIGN PATENT DOCUMENTS

EP      0370636 A1    3/1990

(Continued)

OTHER PUBLICATIONS

Dengel G., et al., "Image Processing in Swallowing and Speech Research," *ISSN*, 6:1, 1432-0460 (1991).

(Continued)

*Primary Examiner* — Sanjay Cattungal
(74) *Attorney, Agent, or Firm* — Wolf, Greenfield & Sacks, P.C.

(57) ABSTRACT

A system and method for obtaining a quantitative measurement of the location and size of a contrast material within a bodily organ, such as the GI tract of a person. A contrast material is introduced into the organ and a plurality of images is obtained. A curve representing the bodily organ is formed based on the images. Local image fields are defined along the curve and a field intensity is found for each by integrating the intensity of the image in the field. An intensity profile along the length of the curve is thus obtained for each image and provides a quantitative representation of contrast material along the bodily organ. The profiles are displayed in any suitable way. In some embodiments, identification of the curve may be aided by introduction of targets are into the organ. The target locations can be identified in each image. In some embodiments, an image obtained without the contrast material is subtracted from each of the plurality of images to cancel the background radiopacity and isolate the contrast material in each profile.

34 Claims, 17 Drawing Sheets

U.S. PATENT DOCUMENTS

| | | | |
|---|---|---|---|
| 5,860,923 A | 1/1999 | Lenker et al. | |
| 6,036,682 A | 3/2000 | Lange et al. | |
| 6,110,191 A * | 8/2000 | Dehdashtian et al. | 606/192 |
| 6,210,338 B1 | 4/2001 | Afremov et al. | |
| 6,540,774 B1 | 4/2003 | Cox | |
| 7,169,140 B1 * | 1/2007 | Kume | 604/529 |
| 7,553,323 B1 * | 6/2009 | Perez et al. | 623/1.11 |
| 7,678,100 B2 * | 3/2010 | Chin et al. | 604/533 |
| 8,043,285 B2 * | 10/2011 | Thompson et al. | 606/32 |
| 2001/0003143 A1 | 6/2001 | Addington et al. | |
| 2002/0026149 A1 | 2/2002 | Agro et al. | |
| 2002/0115931 A1 | 8/2002 | Strauss et al. | |
| 2003/0088179 A1 | 5/2003 | Seeley et al. | |
| 2003/0088195 A1 | 5/2003 | Vardi et al. | |
| 2003/0130679 A1 | 7/2003 | Aliperti et al. | |
| 2005/0085903 A1 | 4/2005 | Lau | |
| 2005/0107688 A1 | 5/2005 | Strommer | |
| 2006/0058647 A1 * | 3/2006 | Strommer et al. | 600/434 |
| 2006/0190024 A1 | 8/2006 | Bei et al. | |
| 2007/0167750 A1 | 7/2007 | Niethammer | |
| 2007/0208250 A1 | 9/2007 | Sullivan | |
| 2007/0225701 A1 | 9/2007 | O'Sullivan | |
| 2008/0097188 A1 * | 4/2008 | Pool et al. | 600/409 |

FOREIGN PATENT DOCUMENTS

| | | |
|---|---|---|
| JP | 2001-149360 A | 6/2001 |

OTHER PUBLICATIONS

Imam, H., et al., "Bolus Transit Patterns in Healthy Subjects: A Study Using Simultaneous Impedance Monitoring, Videoesophagram and Esophageal Manometry," *Neuroregulation and Motility*, Cleveland Clinic Foundation, 1 page (2004).

Potratz, J.R., et al. "A Comparison of Swallowing in Three Subjects Using an Interactive Processing System," *Computer-Based Medical Systems, Proc. Fifth Ann. IEEE Symposium*, 14:17, 115-122 (1992).

European Search Report dated Apr. 7, 2011, 8 pages.

International Search Report and Written Opinion mailed Apr. 20, 2009 for International Application No. PCT/US2008/011666 (8 pages).

\* cited by examiner

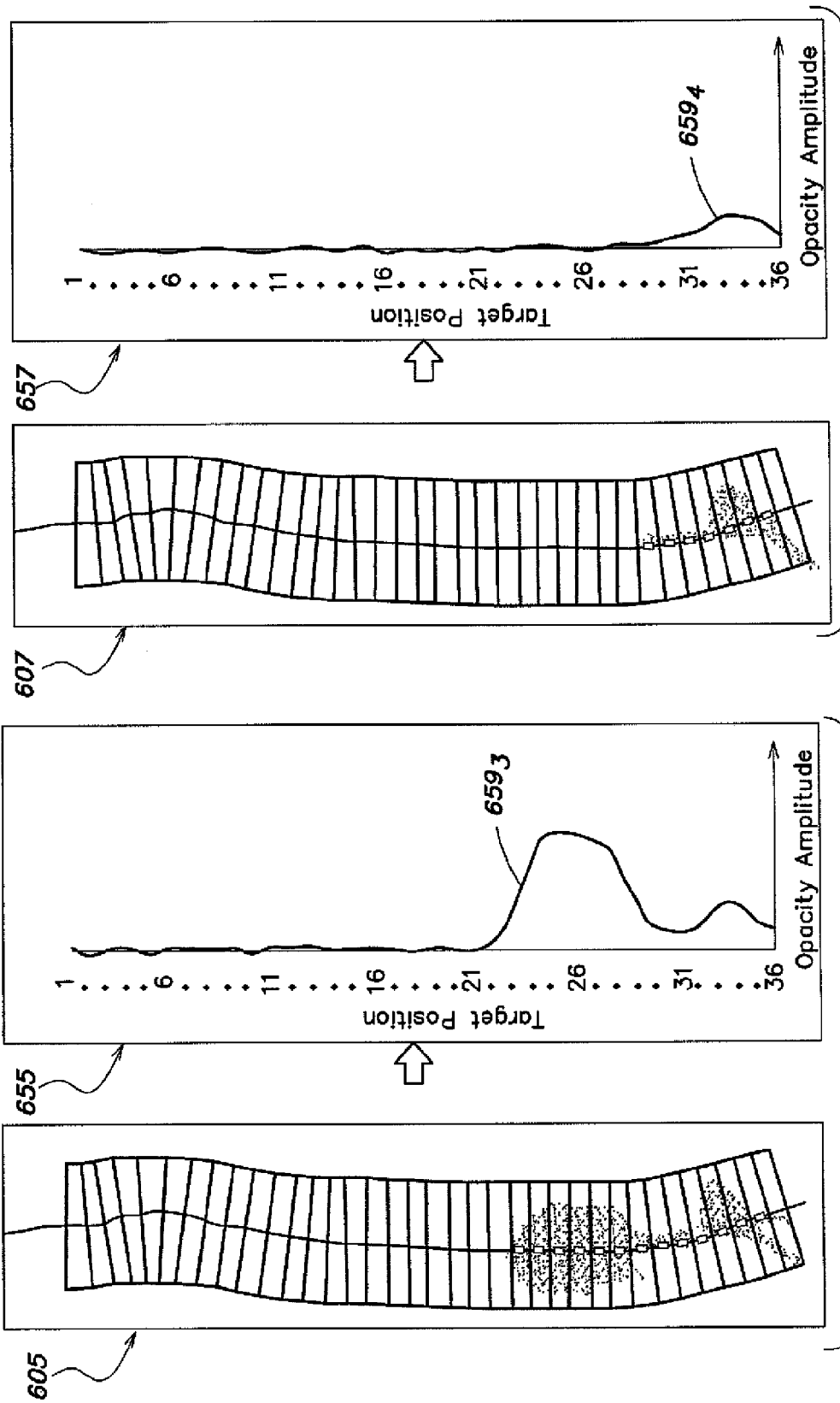

METHOD OF MEASURING AND DISPLAYING THE POSITION OF RADIOGRAPHICALLY CONTRASTED MATERIAL WITHIN LUMINAL BODY ORGANS

CROSS-REFERENCE TO RELATED APPLICATION

The present application claims the benefit, under 35 U.S.C. §119(e), of U.S. Provisional Application Ser. No. 60/998,526, filed Oct. 11, 2007, entitled "Method of Measuring and Displaying the Position of Radiographically Contrasted Material Within Luminal Body Organs," which application is hereby incorporated herein by reference.

BACKGROUND

A variety of medical imaging technologies have been developed to produce diagnostic images of the interior of the human body. Radiography is frequently used for this purpose, and fluoroscopy is one technology that allows for real time imaging of structures in motion. Fluoroscopic images are formed by measuring the intensity of radiation passing through the patient. The intensity varies with the radiopacity of the imaged region of the patient such that the intensity is representative of the structure of the imaged regions. For fluoroscopic imaging, the intensity of the detected radiation is represented as a visible image. Successive images are captured, each one representing a frame of a video image. Such a video image allows motion of the structures in the region of interest to be observed.

The video image may be displayed in real time or may be recorded and/or played back on a monitor for analysis after it is captured. In some procedures, fluoroscopic imaging is used in real time to aid in the positioning of guidewires or stents in bodily lumens. The guidewire or stent may be built with radiopaque markers to absorb or scatter the majority of x-ray radiation such that when imaged, the markers clearly contrast with relatively radiolucent surroundings. The markers may be placed at strategic positions in the guidewire or stent, such as the distal end, to enable a technician to easily determine the location of the device.

It is also known that a contrast material may be introduced into the patient to delineate anatomy as part of a study using fluoroscopic imaging. The contrast material may reveal functioning of blood vessels, the genitourinary system, or the gastrointestinal (GI) tract, for example. Known contrast materials include barium, in the form of barium sulfate (BaSO4), which may be administered orally or rectally for GI tract evaluation, and iodine in various proprietary forms. These contrast materials absorb or scatter significant amounts of x-ray radiation and may be used with real time imaging to demonstrate dynamic bodily processes.

One such dynamic bodily process that has been observed using radiographic imaging with contrast materials is esophageal peristalsis. Esophageal peristalsis refers to the contraction of circular muscles in the esophagus to propel food and drink through the esophagus to the stomach. For a healthy individual, the contractions begin at the upper end of the esophagus and propagate downwardly toward the lower esophageal sphincter (LES). Though, there are medical conditions under which the normal pattern of contractions is interrupted. This conditions include achalasia, dysphagia, diffuse esophageal spasm, ineffective esophageal motility, and hypertensive LES.

SUMMARY

Diagnosis of certain medical conditions may be improved by quantitatively measuring the location and size of contrast material within luminal organs. The location and size of the contrast material may be ascertained by processing images made using known medical imaging techniques. Such measurements may be made by identifying fields within a radiographic image representative of regions of the luminal organ. Intensity within the fields may then be used to derive a quantitative indication of the amount of contrast material at locations, corresponding to the fields, along the luminal organ.

In some embodiments, the fields are identified by introducing into the luminal organ one or more targets detectable in an image. The targets are used to define local image fields representing segments along the luminal organ. When a contrast material is introduced into the luminal organ (e.g., a bolus of suspended barium sulfate within the esophagus during a "barium swallow" study), the radiographic image intensity in these local image fields indicates the position and approximate amount of the contrast material at locations along the luminal organ.

The data from one image may be used to display a profile of the material distribution at a given point in time. If data from successive images is collected, the data may be used to generate a spatiotemporal plot showing detected amounts of the material as a function of both position and time.

Positional information on the bolus may be co-registered with other data relating to the luminal organ and displayed for analysis. For example, pressure data representing muscular contractions may be displayed co-registered with bolus positional information to enhance study of the luminal organ or diagnosis of a patient.

In some aspects, the invention relates to a method of collecting diagnostic data. The method comprises capturing a series of frames at each of a plurality of successive times, the frames comprising radiographic imaging data of a bodily lumen of a patient as a radiographic contrast material transits through the lumen; processing the series of frames to compute a plurality of fields, each field being representative of a region along the lumen, and for each frame, computing a quantitative indication of an amount of the contrast material; and providing as an output a quantitative indication of the amount of the contrast material at each of a plurality of locations along the bodily lumen as a function of time based on the computed quantitative indications.

In another aspect, the invention relates to a system for collecting diagnostic data. The system comprises a computing device and a display device. The computing device is configured to receive a plurality of radiographic images from a radiographic imaging system, each of the plurality of images representing a region containing a plurality of radiopaque targets and a contrast material, each radiopaque target associated with a location in the radiographic image, and configured to compute a plurality of values from each radiographic image, each value being computed from at least an intensity of the radiographic image in a local image field for a position along a path, the path being based on at least the locations of the plurality of radiopaque targets. The display device is configured to display the plurality of values as a function of the position along the path for each of the plurality of radiographic images.

In another aspect, the invention relates to a system comprising a computing device and a display device. The computing device is configured to receive an image from an imaging system, the image representing a region containing a target and a contrast material, and configured to compute a plurality of values from the image, each value being computed from at least an intensity of the image in a local image field for a position along a path, the path being based on at least a location of the target in the image. The display device is configured to display the plurality of values as a function of the position along the path.

In yet another aspect, the invention relates to a computer storage medium comprising computer executable instructions that, when executed on a computer, perform a method of processing diagnostic data using frames from a radiographic imaging system, the frames comprising intensity data indicative of attenuation of radiation passing through a bodily lumen of a patient, the frames being acquired at a plurality of successive times during which a member is present in the lumen, the member comprising a plurality of radiopaque regions identifiable in the frames. The method comprises, for each frame, determining within the frame a plurality of fields, each field representing a region around a corresponding radiopaque region of the plurality of radiopaque regions; for each field of the plurality of fields within the frame computing, based on the intensity within the field, a value indicative of a quantity of contrast material in the frame; and associating in computer storage media coupled to the computer the computed value indicative of the quantity with a spatial position along the lumen, the lumen being based on the position of the corresponding radiopaque region along the member.

BRIEF DESCRIPTION OF DRAWINGS

The invention and embodiments thereof will be better understood when the following detailed description is read in conjunction with the accompanying drawing figures. In the figures, elements are not necessarily drawn to scale. In general, like elements appearing in multiple figures are identified by a like reference designation. In the drawings:

FIG. 4D is a radiographic image of a catheter having three radiopaque targets inside a bodily lumen with elliptical local image fields constructed and superimposed;

FIGS. 6A-6D illustrates a series of 4 radiographic images and corresponding profiles when the baseline image is subtracted from each of the series of images;

DETAILED DESCRIPTION

Figure 1:
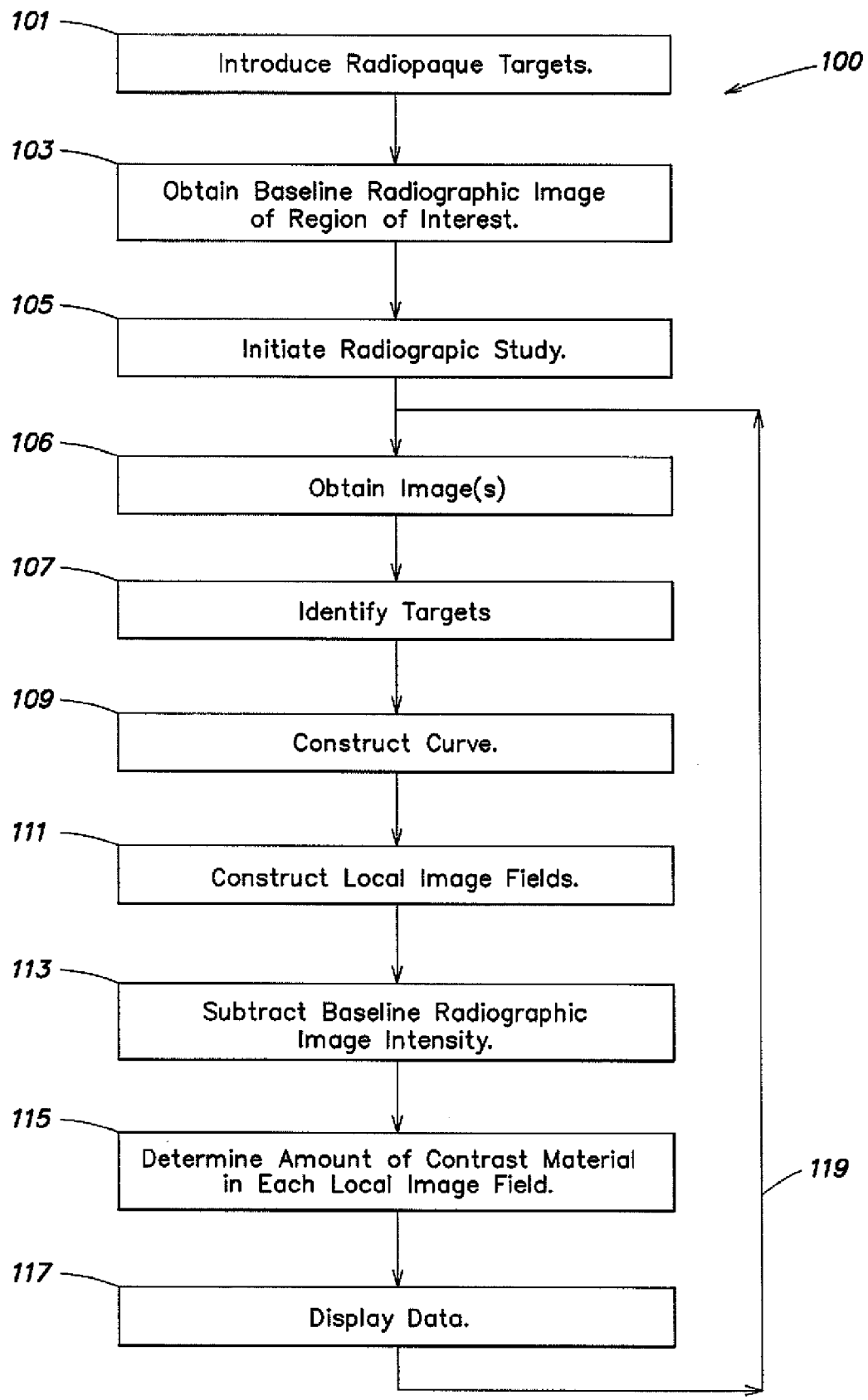
FIG. 1 is a flow chart illustrating method of collecting diagnostic data according to some embodiments.

The inventor has recognized an appreciated that new insights into the physiology and pathophysiology of bodily organs in general and in individual clinical cases may be obtained through analysis and display of medical imaging data. Such insights may be obtained through quantitative measurements of the location and size of contrast material within a luminal organ determined using medical imaging and new image processing and display techniques.

To obtain and analyze data, radiopaque targets may be introduced into the bodily lumen to serve as reference points in the radiographic image. The reference points may be used for the construction of local image fields in which the intensity of the image (e.g., brightness, opacity) is measured. The image intensity within the fields is indicative of the amount of the contrast material at locations along the lumen. Movement of the contrast material may be quantitatively tracked over time from a sequence of radiographic images. Suitable methods for displaying the quantitative measurements enable a quicker and more reliable diagnosis of certain disorders of the luminal organ, such as motility disorders.

In some embodiments, radiopaque targets may be fixed along the length of a catheter which is introduced into the bodily lumen. A radiographic image may be taken before introduction of the contrast material to determine the background or baseline intensity. Contrast material is then introduced into the lumen and radiographic images are sequentially captured to observe the movement of the contrast material. The catheter may also carry sensors that can be used to collect data about the bodily lumen, such as pressure data.

This data may be co-registered temporally and spatially with the bolus position information extracted by processing the radiographic image. As a result, the data may be displayed or otherwise processed together.

The images may then be processed in real time or after the procedure to quantitatively measure the location and size of the contrast material. For each radiographic image taken, the radiopaque targets may be automatically or manually identified in the image. For example, detection via the shape and contrast of the radiopaque targets may be used as a basis of a suitable identification algorithm. A curve may be constructed that connects in sequence a key characteristic of the radiopaque targets (e.g., their image centroids). The curve may then be subdivided into segments and local image fields associated with each segment. In each local image field the intensity in the local image field may be measured by integrating the image intensity within the field. In some embodiments, the baseline intensity, determined from the baseline radiographic image, may be subtracted to enhance the contrast of the contrast material.

For each radiographic image, a profile of the contrast material may be constructed from the intensity measurements determined from the local image fields as a function of the position of the local image field along the curve. The profiles may then be presented in any suitable way for analysis and diagnosis. For example, the profiles may be individually plotted, animated, or displayed as part of a spatiotemporal plot.

A method 100 of collecting diagnostic data according to some embodiments is described with reference to the flow chart of FIG. 1.

In step 101, one or more radiopaque targets are introduced into a region of interest, such as a bodily lumen. Targets may be made of any suitable material, such as a metal or metal-containing film or compound. Of course, the suitability of a material may depend on the energy of radiation used for imaging.

The targets are made relatively fixed with respect to one another and the lumen. The targets may be incorporated along the length of a substrate, such as a catheter used to introduce the targets into the bodily lumen.

In some embodiments, the catheter may contain sensors, which may act as targets. In other embodiments, targets may be located adjacent to the sensors. For example, in embodiments used for manometry studies, a catheter may include pressure sensors which also serve as radiopaque targets.

In step 103, a baseline image covering a region of interest is taken. Any suitable instrument may be used to obtain the radiographic image. For example, a radiographic image may be formed using a fluoroscope or any other suitable imaging system. The radiographic image may be a monochromatic image. For example, the radiographic image may be represented in grayscale, with radiopaque points indicated with black, and radiolucent points indicated with white. In such an image the radiopaque targets will appear as dark portions.

The baseline radiographic image may be taken before a contrast material is introduced into the lumen such that variations in the image intensity (aside from the radiopaque targets) may be attributed to the properties of the lumen and surrounding bodily structure. This background intensity may stay relatively constant during the radiographic study.

Figure 2A:
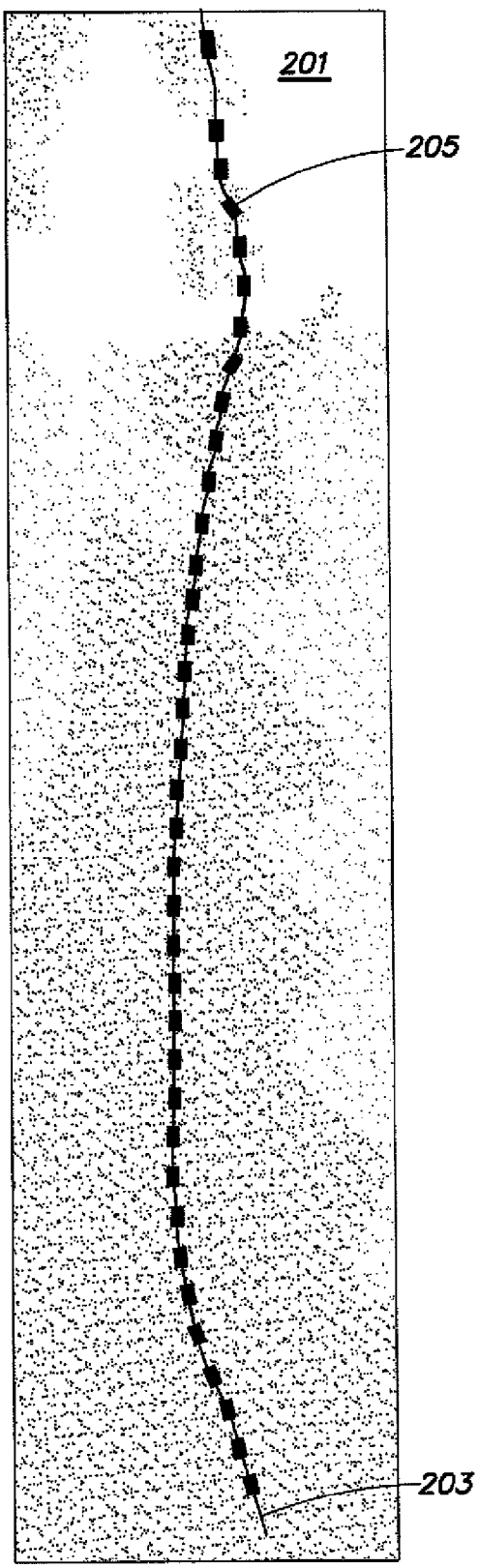
FIG. 2A is a radiographic image of a catheter having 36 radiopaque targets inside a bodily lumen.
Figure 4A:
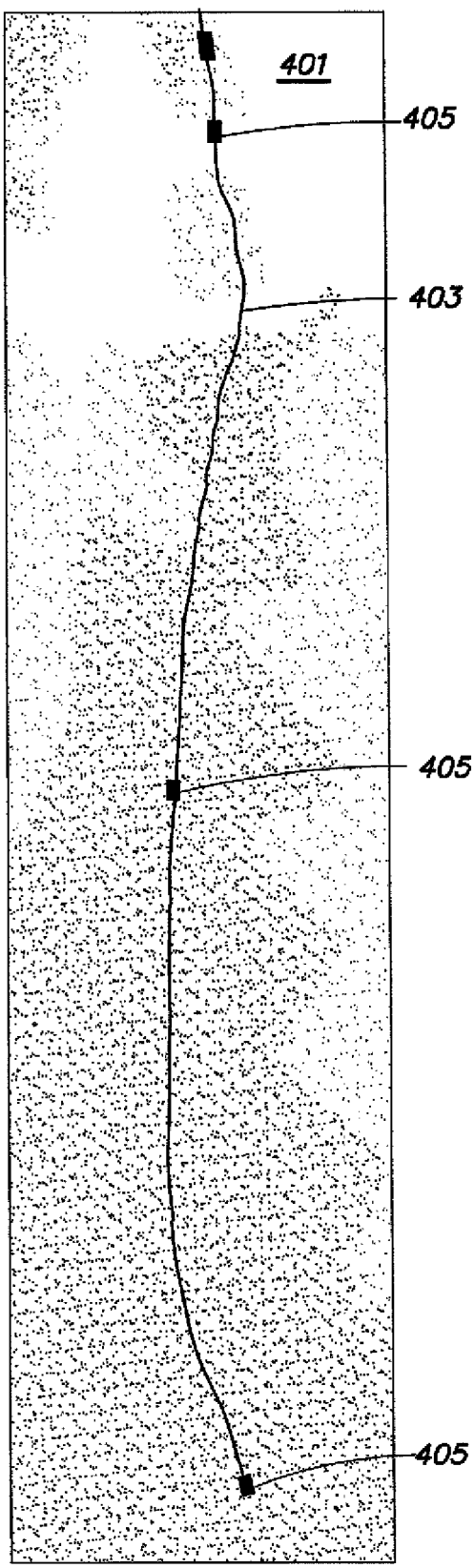
FIG. 4A is a radiographic image of a catheter having three radiopaque targets inside a bodily lumen.

FIG. 2A is an example of a baseline image 201 acquired in step 103. Clearly visible in the example image 201 are a catheter 203 having 36 radiopaque targets 205 positioned inside a bodily lumen. Another example of a baseline image is shown in FIG. 4A. Here catheter 403 has only 3 targets 405.

Figure 9A:
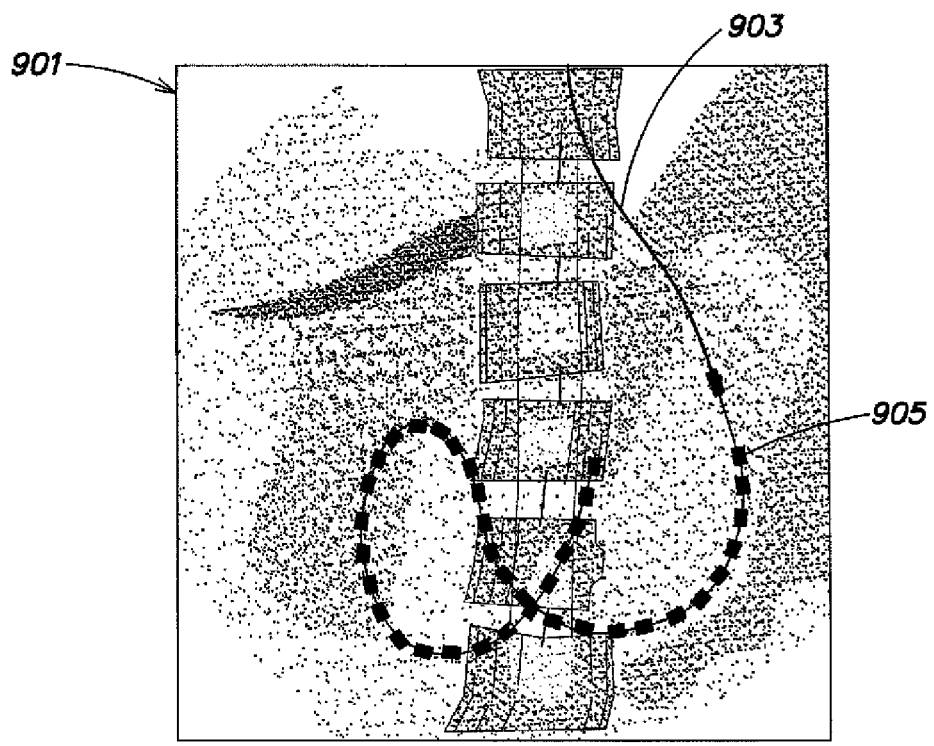
FIG. 9A is a radiographic image of a catheter inside a bodily organ with a convoluted path.

Yet another example is shown in FIG. 9A where a catheter 903 and associated targets 905 has assumed a convoluted shape.

Returning to FIG. 1, in step 105, a radiographic study is initiated. The study may be conducted as is known in the art, which may include initiating passage of a contrast material through the lumen. If for example, the radiopaque targets have been distributed within the esophagus of a patient, a barium swallow or other suitable bolus may be used.

During the radiographic study, a series of radiographic images are taken (step 106), for example, using the same instrument used in step 103. The images may be taken sequentially to capture, for example, the movement of the contrast material. A suitable fixed frame rate or irregular frame rate may be used. Images may be time stamped to enable proper temporal reconstruction.

Steps 107, 109, 111, 113, 115, and 117 may be performed for each image in the series. In some embodiments, these steps may be performed in real time. For example, the steps may be pipelined, or performed before returning via return path 119 to step 106 to obtain another image. Alternatively, the steps may be performed at any suitable later time. For example, after the diagnostic procedure has been performed. In some embodiments, radiographic images are processed post hoc based on stored data. In yet other embodiments, radiographic images are processed during a study and may be processed again post hoc.

Figure 2B:
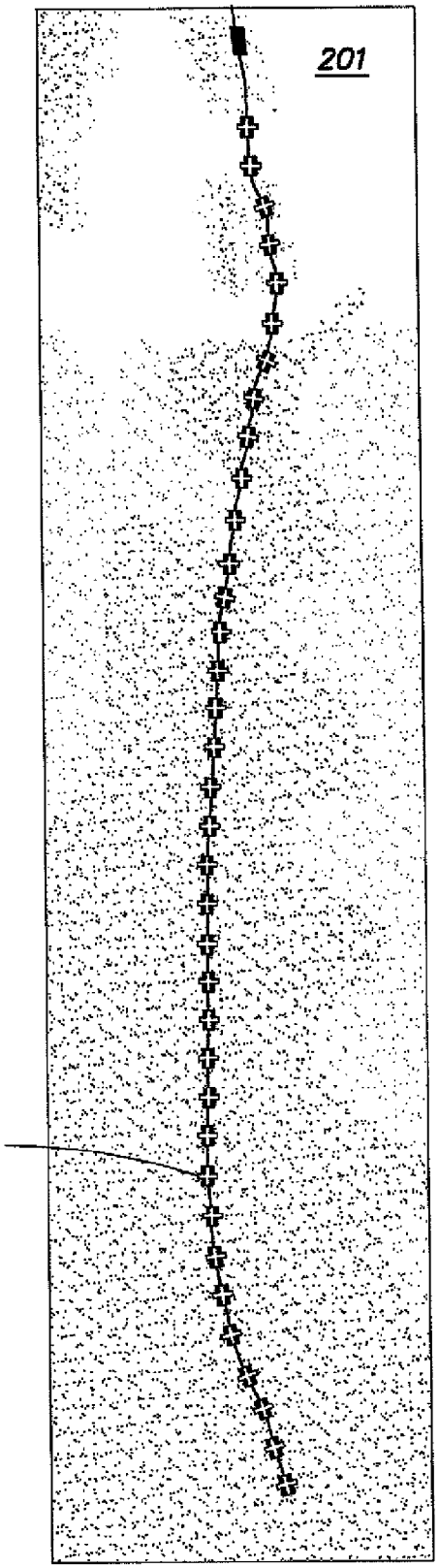
FIG. 2B is a radiographic image of a catheter having 36 radiopaque targets inside a bodily lumen with the location of the radiopaque targets indicated by superimposed crosshairs.
Figure 4B:
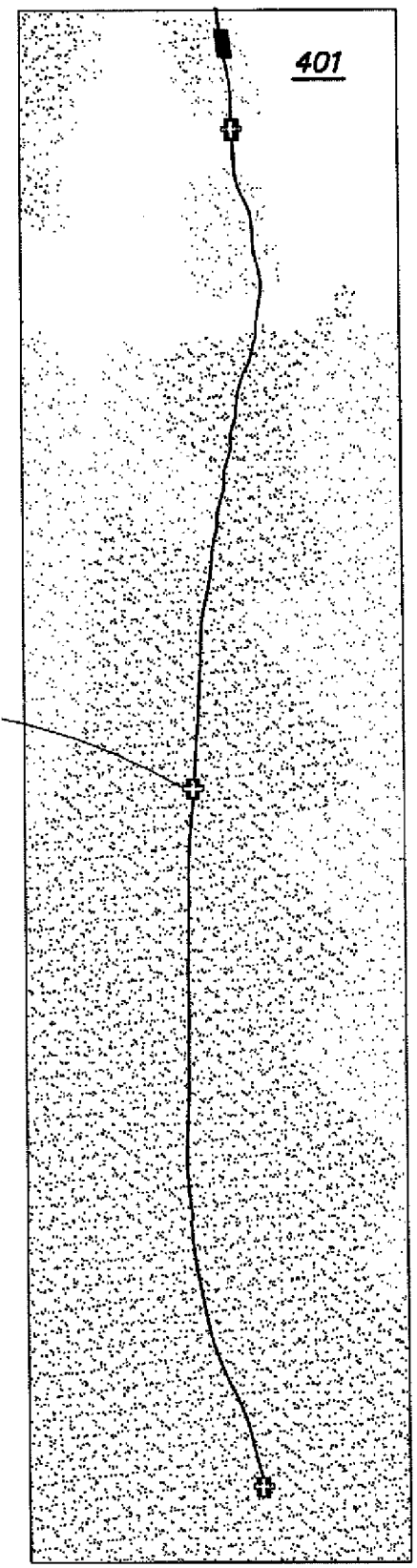
FIG. 4B is a radiographic image of a catheter having three radiopaque targets inside a bodily lumen with the location of the radiopaque targets indicated by superimposed crosshairs.
Figure 9B:
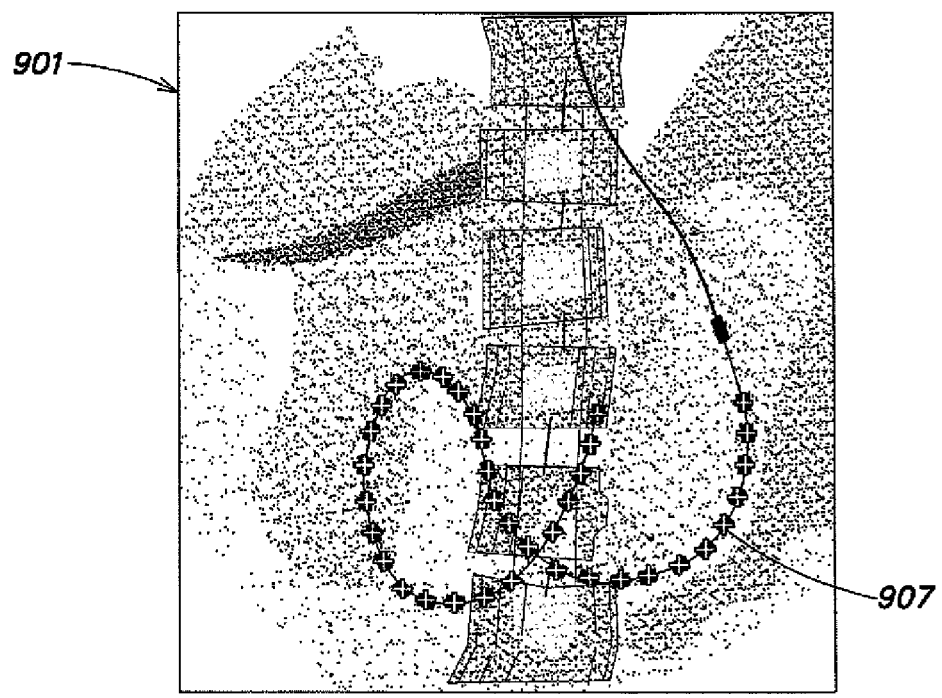
FIG. 9B is a radiographic image of a convoluted catheter inside a bodily organ with the location of the radiopaque targets indicated by superimposed crosshairs.

For each radiographic image the locations of the radiopaque targets introduced in step 101 are identified (step 107). A computer system may be programmed with a suitable algorithm for identifying the targets or configured to permit manual identification. Once a location of a target is generally identified, a key characteristic of the targets may be used to identify a precise position. For example, the position may be defined by the target's image centroid. FIG. 2B show an example where the positions of the radiopaque targets 205 in radiographic image 201 are identified with crosshairs 209. Similarly, target positions are identified with crosshairs 407 and 907 as shown in FIGS. 4B and 9B, respectively.

Figures 3A, 3B:
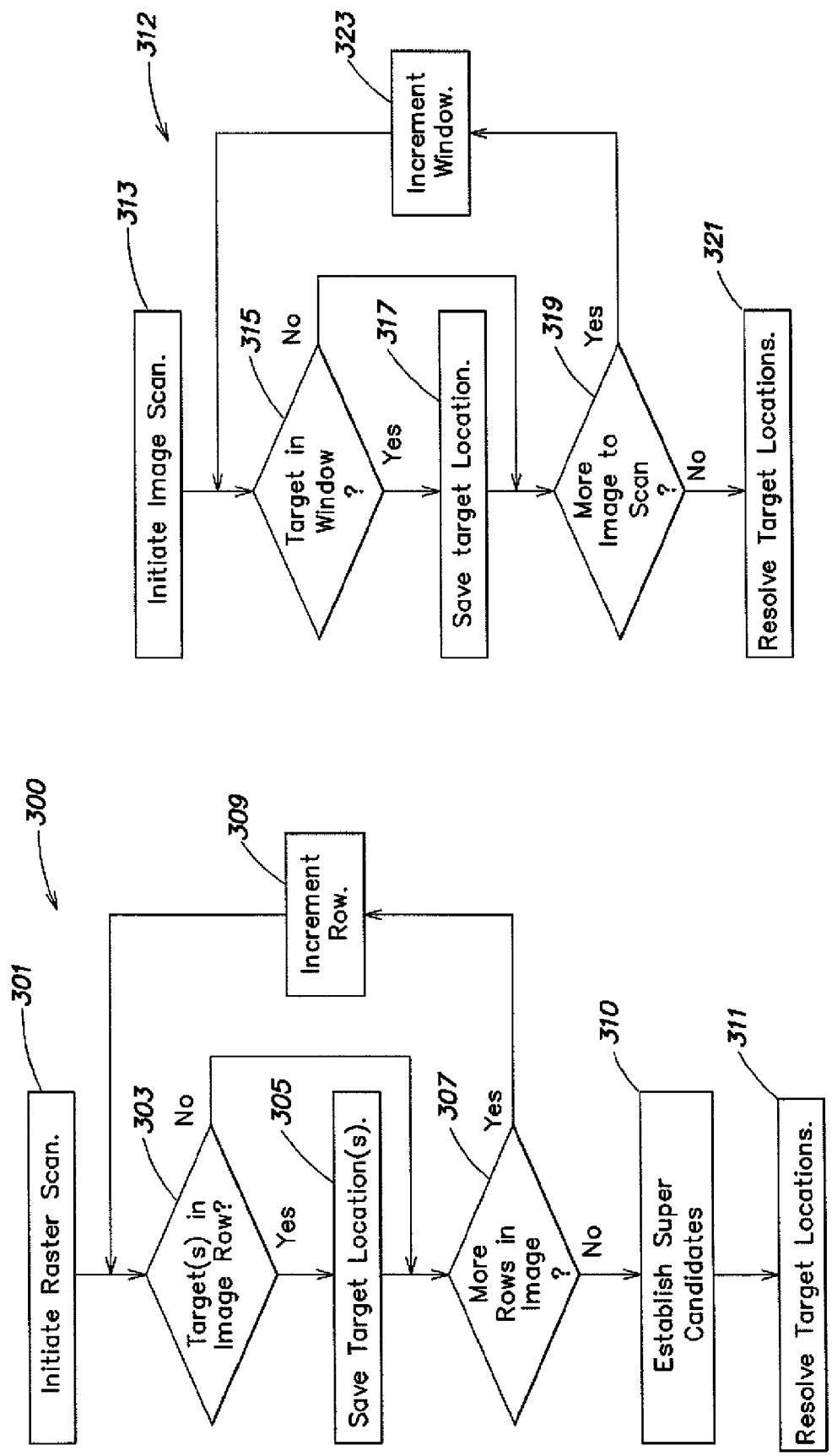
FIG. 3A is a flow chart illustrating method of determining the locations of the targets according to one embodiment.
FIG. 3B is a flow chart illustrating method of determining the locations of the targets according to another embodiment.

Many possible routines may be used to identify target locations autonomously and any suitable routine may be used. As one example, FIG. 3A provides a method 300 for identifying target locations by raster scan. The routine scans one or more rows of the image for changes in image intensity indicative of a radiopaque target. The rows being scanned are incremented until all targets are found or the entire image has been scanned. At step 301, the raster scan is initialized and various parameters may be set. For example, the parameters may include the image to be scanned, minimum and maximum target diameter, brightness threshold, rows to simultaneously scan, and number of rows per increment. At step 303 a next row(s) (e.g., initially the top row or rows) of the image is scanned to identify candidate targets. Candidate targets may be identified as those areas corresponding to a change in image intensity, along the scanned row or set of rows, above a specified threshold followed by a change in the reverse direction where the distance between the changes is not greater than the maximum target diameter. If targets are in the row, the target locations are saved (step 305). If there are more rows to investigate (step 307), the rows to be scanned are updated (step 309) and the identification process is repeated (step 303).

In the embodiment illustrated, once all rows are scanned for candidate target locations, "super candidate" target locations may be identified at step 310. Super candidate target locations may be defined as contiguous candidate locations in adjacent rows. The number of adjacent rows in which a candidate target location is present before a target location is identified as a super candidate may be determined in any suitable way. For example, the number of rows may be specified by a user or determined from the target sizes and image resolution.

Though, the timing at which super candidate locations are identified may be varied. For example, after each sequential row is scanned, the target locations for the row may be analyzed with the target locations from previously scanned rows to identify super candidate target locations.

The super candidate locations may then be further discriminated in step 311 by a variety of algorithmically implemented constraints including: being not more than the maximum target size, having the candidate target shape (and rotations thereof), having a known target spacing, and lying along a curve consistent with the minimum bend radius of the catheter to which the targets may be attached and/or tubular organ under study. In the embodiment illustrated, those candidate target locations that are not part of super candidate location are not further processed.

Processing at step 311 may further include refining the target location. In some embodiments, a key characteristic of a target in combination with the target shape may be used to define the target location. For example, a center of mass calculation may be used to determine the center of each target identified. Additionally, the targets may be ordered for the subsequent forming a curve in step 109 (FIG. 1).

As a second example, FIG. 3B provides a method 312 for identifying the targets using a window slightly larger than the maximum target size. At step 313, the routine is initialized and initial parameters such as window position, size, and scan path may be specified. For each position a determination is made of the presence of a target in the window (step 315). Targets may be recognized for example, by size, contrast, and/or shape. If a target is present, the target position is saved (step 317) and if there is more image to scan (step 319) the window position is incremented (step 323). The process is repeated for each window position until the entire image has been scanned or all targets detected. By making the increment of window movement sufficient small, it can be assured that each target will lie in the window at least once. Optionally, step 321 may be performed to resolve any ambiguities or duplicates in target locations and to order targets as in step 311.

Additionally, or as yet another alternative, a graphical user interface (GUI) may be provided for a user to manually identify target locations. For example, a GUI may be constructed in which the user simply positions a cursor over each visual is identified target and designates its position (e.g., using a mouse or trackball). Such a GUI may also be used to review and correct positions identified automatically.

Figure 2C:
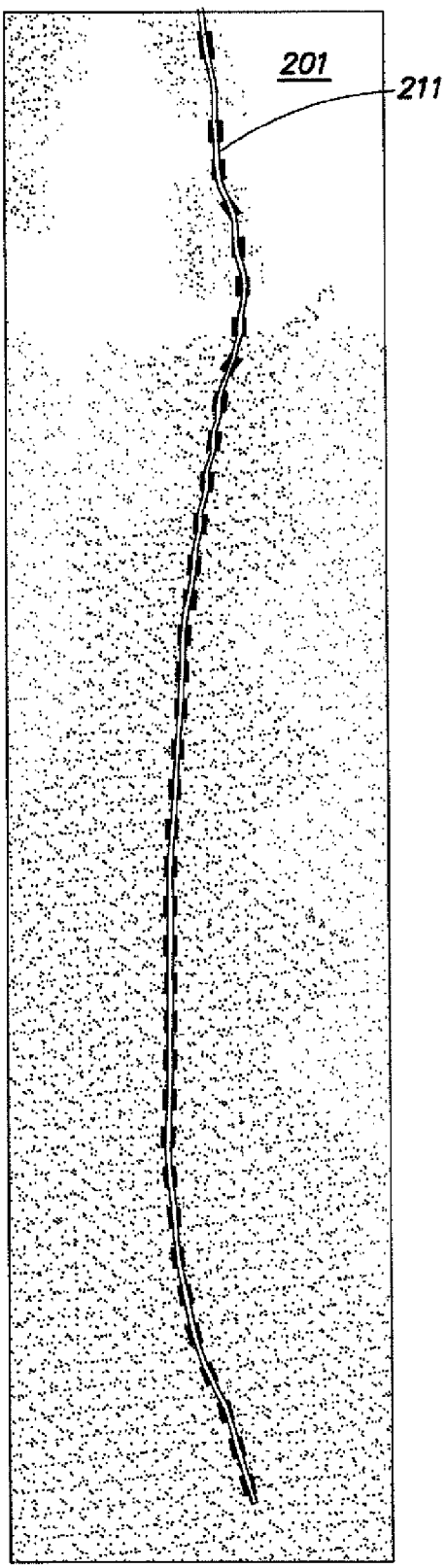
FIG. 2C is a radiographic image of a catheter having 36 radiopaque targets inside a bodily lumen with a curve obtained from the location of the radiopaque targets superimposed.
Figure 4C:
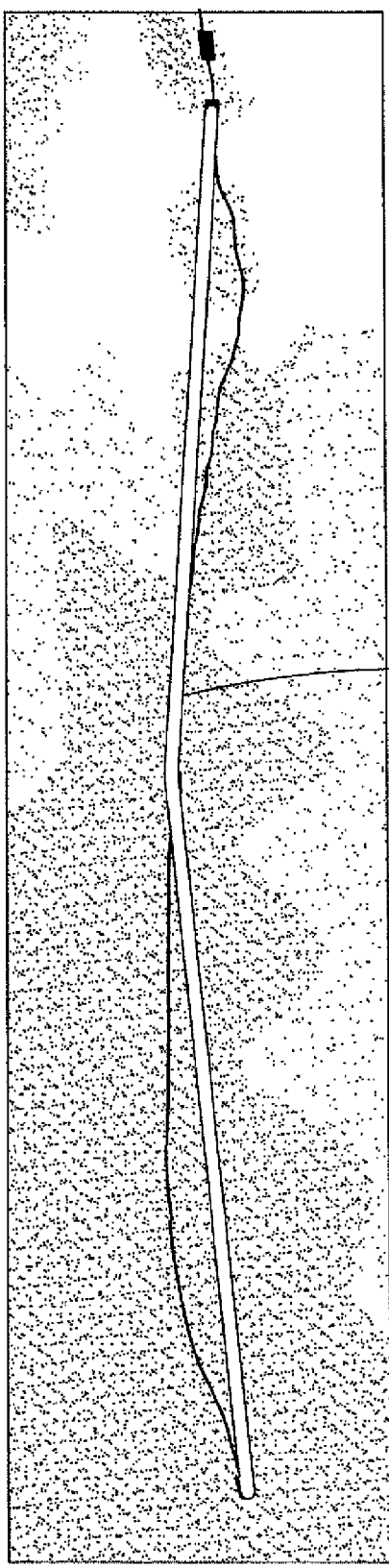
FIG. 4D is a radiographic image of a catheter having three radiopaque targets inside a bodily lumen with a curve obtained from the location of the radiopaque targets superimposed.
Figure 9C:
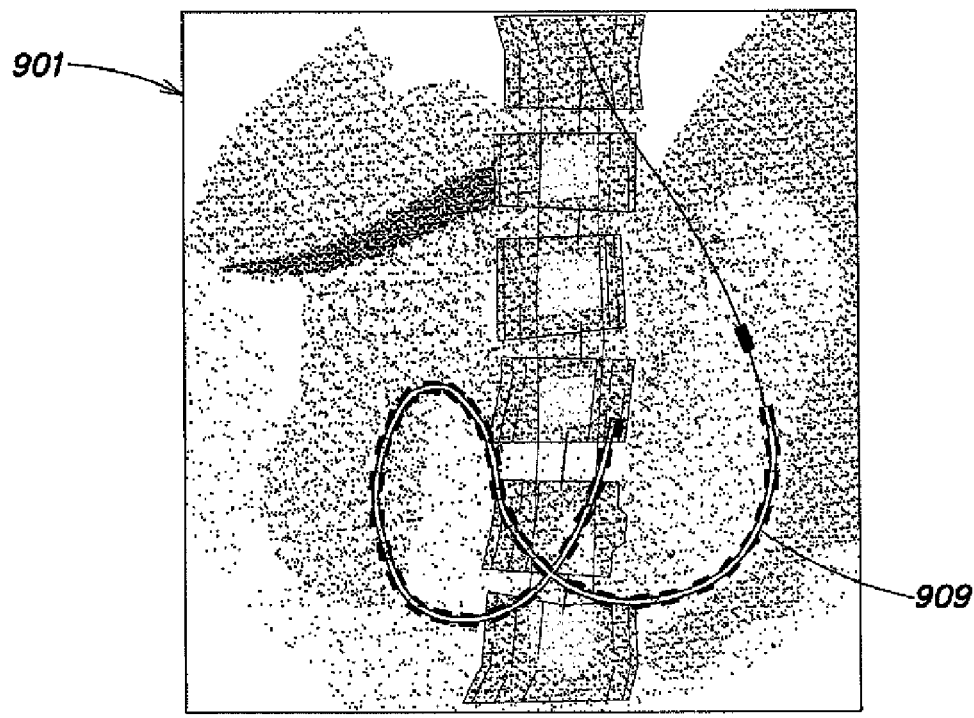
FIG. 9C is a radiographic image of a convoluted catheter inside a bodily organ with a curve obtained from the location of the radiopaque targets superimposed.
Figure 9D:
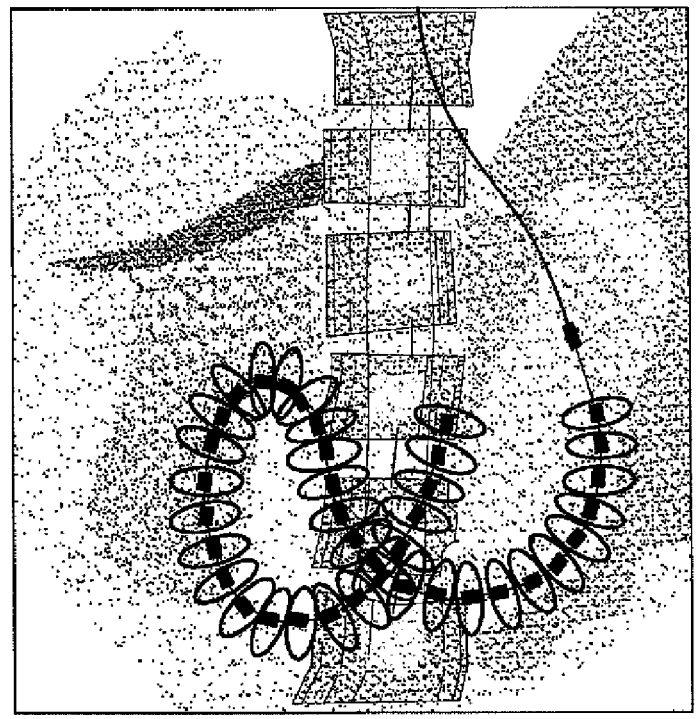
FIG. 9D is a radiographic image of a convoluted catheter inside a bodily organ with elliptical local image fields constructed and superimposed.

Returning to FIG. 1, in step 109 of method 100, a curve is constructed based on the positions of the targets. Any suitable curve forming algorithm may be used. FIG. 2C provides an example in which a curve 211 is constructed to pass through each of the target locations 209 (FIG. 2B). In some embodiments, a polynomial curve fitting technique may be applied to the array of target positions. Some curve forming algorithms may require the sequence (i.e., order) of targets be specified to ensure the fitting algorithm correctly connects sequential targets. The appropriate sequence may be determined, for example, based on a known target spacing along a catheter. For example, one suitable algorithm constructs a curve from a series of lines connecting the locations of targets adjacent in the sequence, such as for curve 409 of FIG. 4C. Other situations, such as that shown in FIG. 9C, may require slightly more sophisticated curve forming algorithm. For example, it is clear from the image 901 that the curve 909 may be correctly resolved by setting a minimum radius of curvature.

In step 111, local image fields are constructed along the curve formed in step 109. Each local image field defines a region of the radiographic image within which a measurement of image intensity is made. There are a large number of suitable possibilities for defining local image fields and any suitable technique may be used. Several illustrative examples are provided such that an order resulting in a curve with a radius of curvature less than the minimum may be deemed unlikely and otherwise possible curves may be constructed.

Figure 2D:
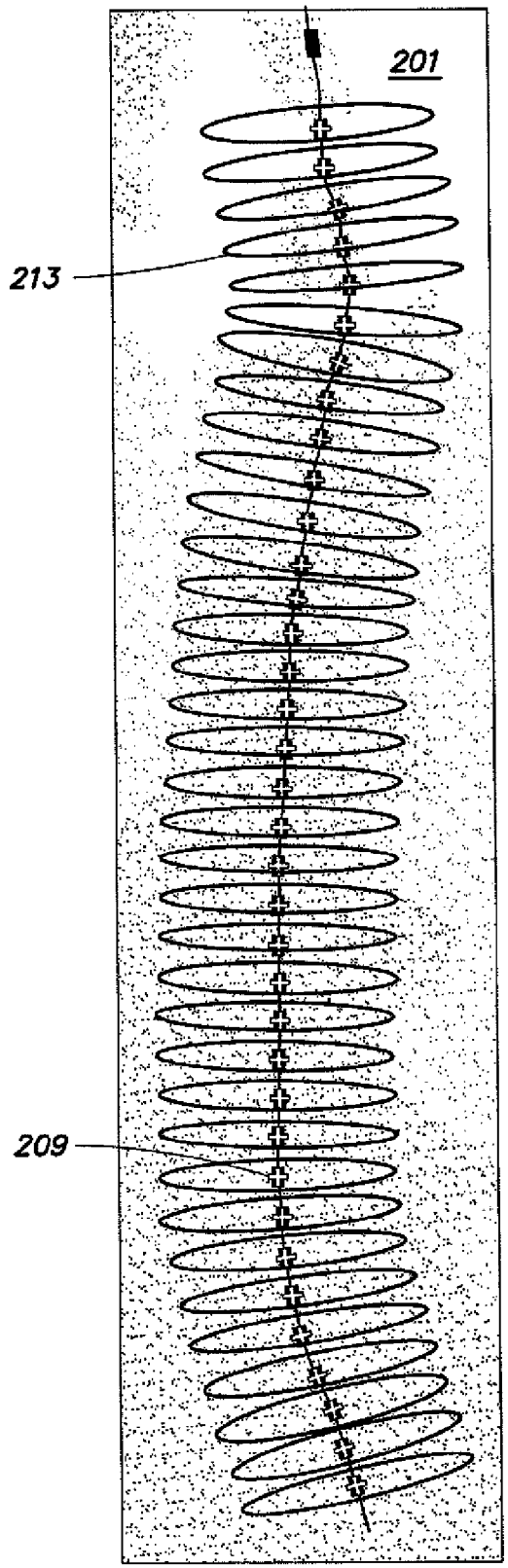
FIG. 2D is a radiographic image of a catheter having 36 radiopaque targets inside a bodily lumen with elliptical local image fields constructed and superimposed.
Figure 5A:
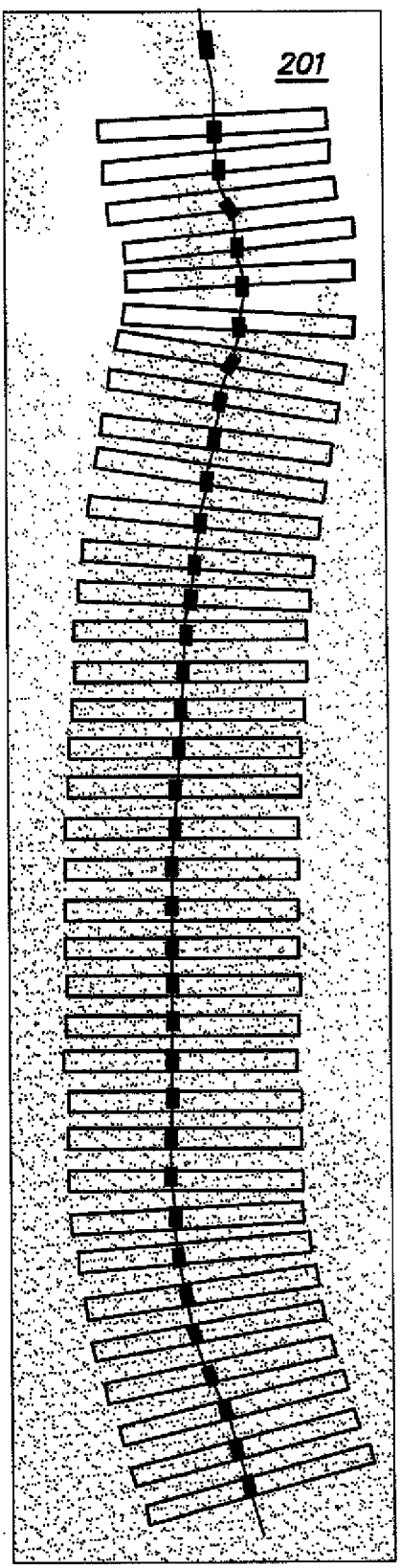
FIG. 5A is a radiographic image of a catheter having 36 radiopaque targets inside a bodily lumen with rectangular local image fields constructed and superimposed.

In some embodiments, local image fields are constructed at each target location as in the example shown in FIG. 2D. Local image fields 213 are illustrated as ellipses with the major axis of the ellipse normal to the curve 211 centered at the target locations indicated by crosshairs 209. However, any suitable shape or orientation may be used. For example, in FIG. 5A rectangular image fields are defined with centers at the target locations and with a long dimension normal to the curve at the associated target point.

Figure 4D:
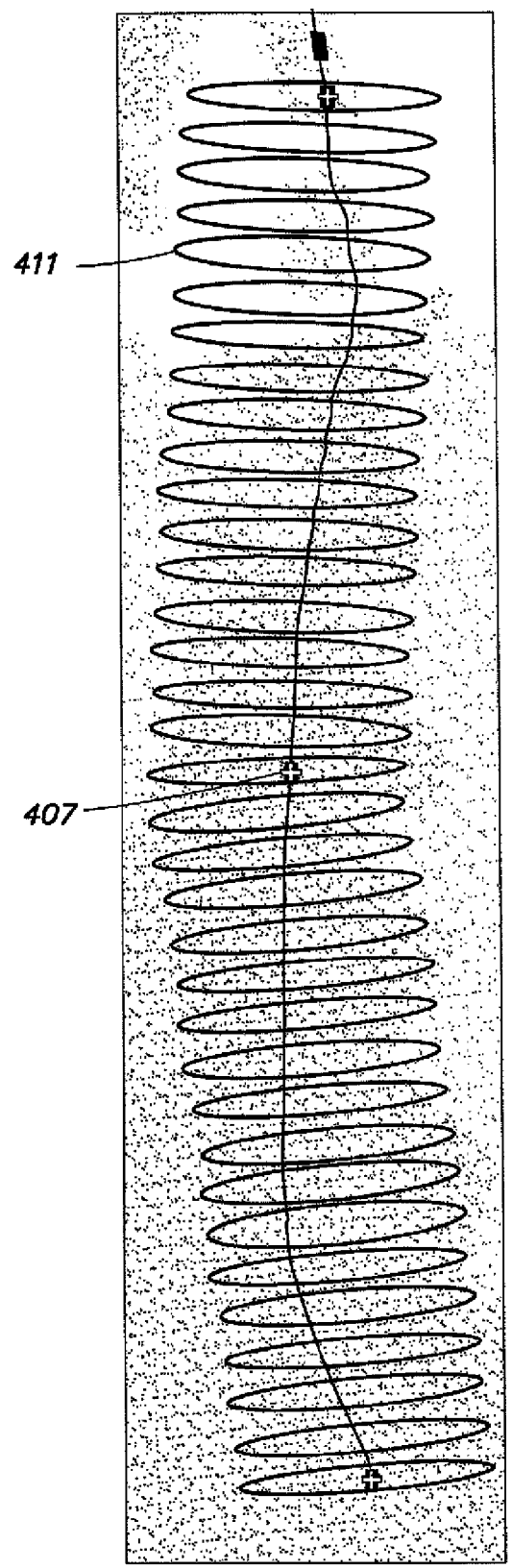

In some embodiments, a different number of targets and local image fields may be desired. Local image fields may be associated with points defined along the curve irrespective of the target locations. These points may serve as reference locations for local image fields. For example, in some embodiments the number of identified or available targets may be less than the number of desired local image fields. Radiographic image 401 shown in FIGS. 4A-4D illustrates such an example. A suitable number of points are defined along curve 409 (FIG. 4C) and a local image field is defined for each point. FIG. 4D shows the constructed local image fields 411. As in FIG. 2D, the local image fields are illustrated as ellipses but here the major axis of each ellipse is normal to the curve at the corresponding reference point rather than a target location.

Figure 5B:
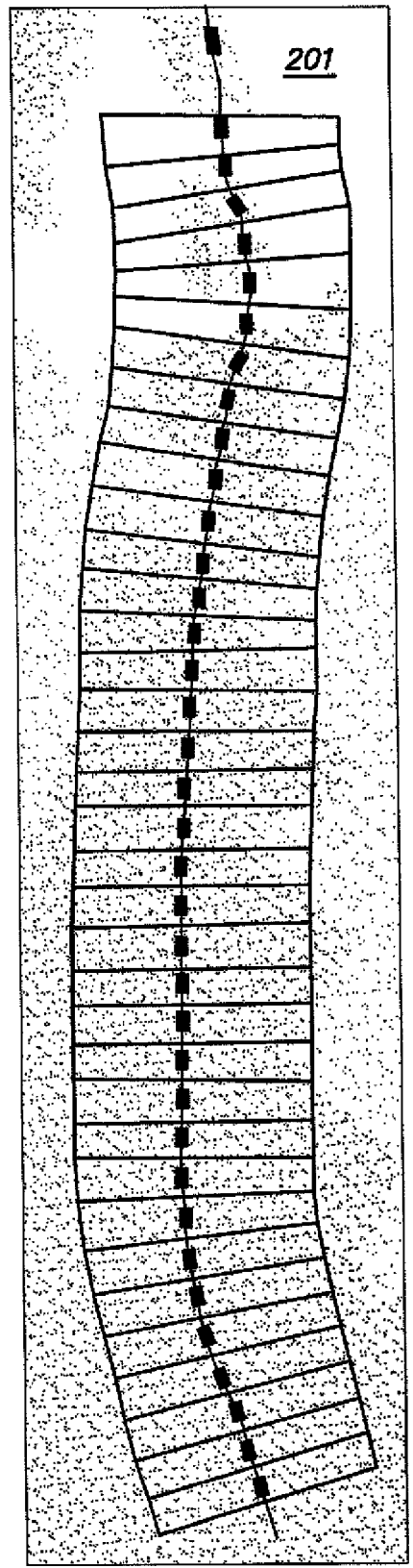
FIG. 5B is a radiographic image of a catheter having 36 radiopaque targets inside a bodily lumen with a local image fields constructed with a ladder structure and superimposed.

Any suitable shape and technique may be used to define the local image fields. FIG. 5B illustrates an alternative construction of the local image fields with radiographic image 201, originally introduced in FIG. 2A. In FIG. 5B, lines of equal length are centered on and normal to the curve between the target locations. The lateral ends of each field are formed by interconnecting the ends of the equal length lines as shown to form closed regions that define local image fields. The local image fields in this example have the appearance of a ladder-type structure. Each quadrilateral region is the local image field associated with the target location at or near its center. This particular example ensures that all the area within a specified distance from the curve is covered by the fields and that there is no overlap among the fields when the radius of curvature of the curve is sufficiently small (or equivalently the lines perpendicular to the curve are sufficiently short).

In step 113, the baseline intensity, determined from the baseline radiographic image obtained in step 103, is optionally subtracted for each radiographic image. The subtraction provides a correction of the baseline offset residual in each image and may enhance the contrast of the contrast material. Two example embodiments of step 113 are provided. However, it should be appreciated that step 113 may be performed in any suitable way. The first is described presently, and the second is described after the description of step 115.

In a first example embodiment of step 113 the baseline radiographic image in the entire region of interest is subtracted from each radiographic image in the series. For example, if the baseline image and each image in the series are of the same size and resolution, the intensity values of each pixel may be subtracted on a pixel by pixel basis.

In step 115, for each radiographic image, the intensity of the image in each local image field is determined in any suitable way. In some embodiments, the image intensity within the local image field is integrated over the local image field area to determine the field intensity. For example, for a pixilated image the pixel value of all pixels within a given local image field may be summed, the sum representing the field intensity. In some other embodiments, the integral may be weighted by the total area of the local image field, for example, by dividing the integral by the area of the local image field (e.g., the number of pixels in the field). This may be useful, for example, when the local image fields are not of uniform size (e.g., as with the ladder structure). The field intensity is indicative of the size of the contrast material in the vicinity of the reference point associated with the local image field.

Figure 5C:
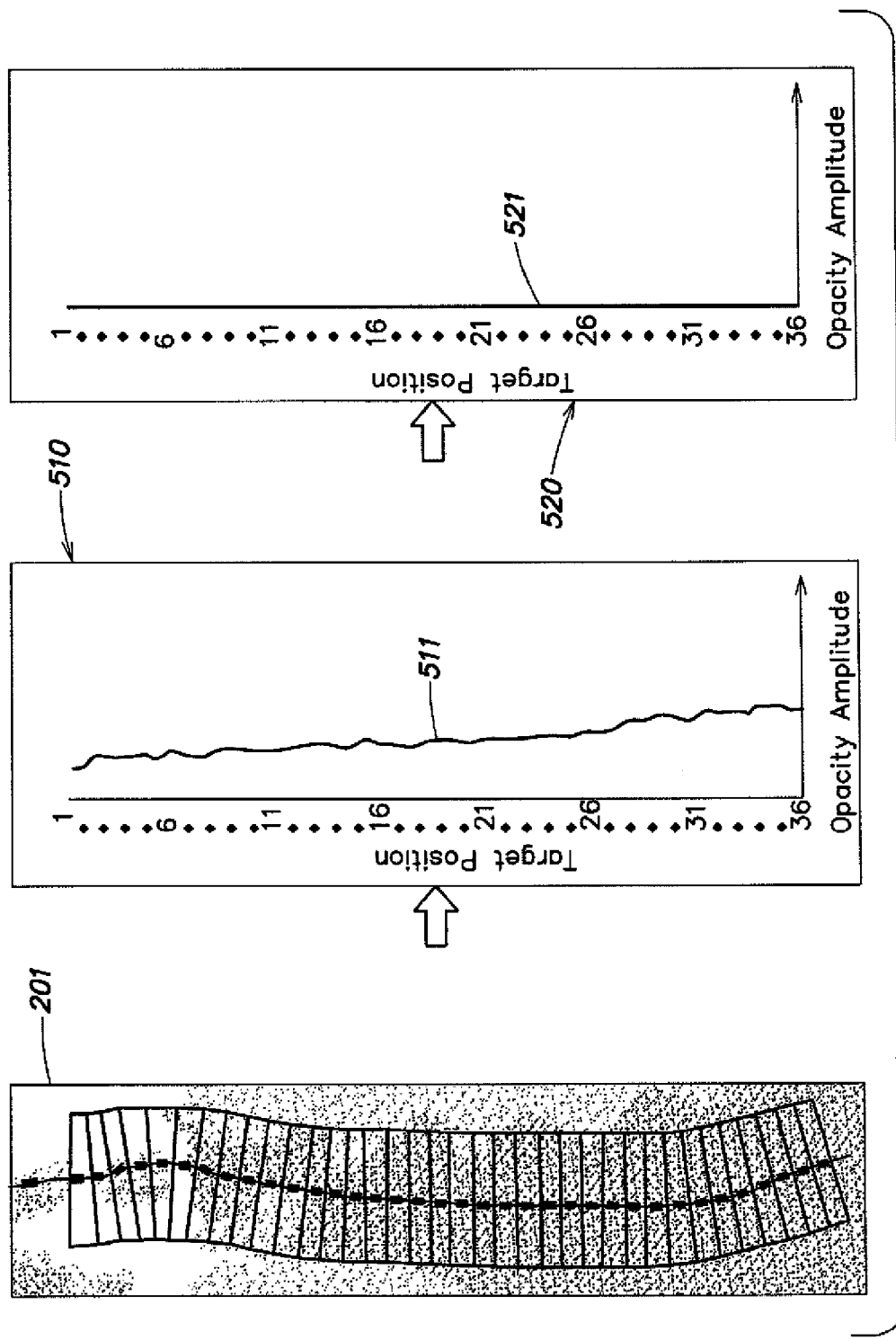
FIG. 5C is a series of images illustrating the cancellation of the baseline image using local image fields.
Figure 6A:
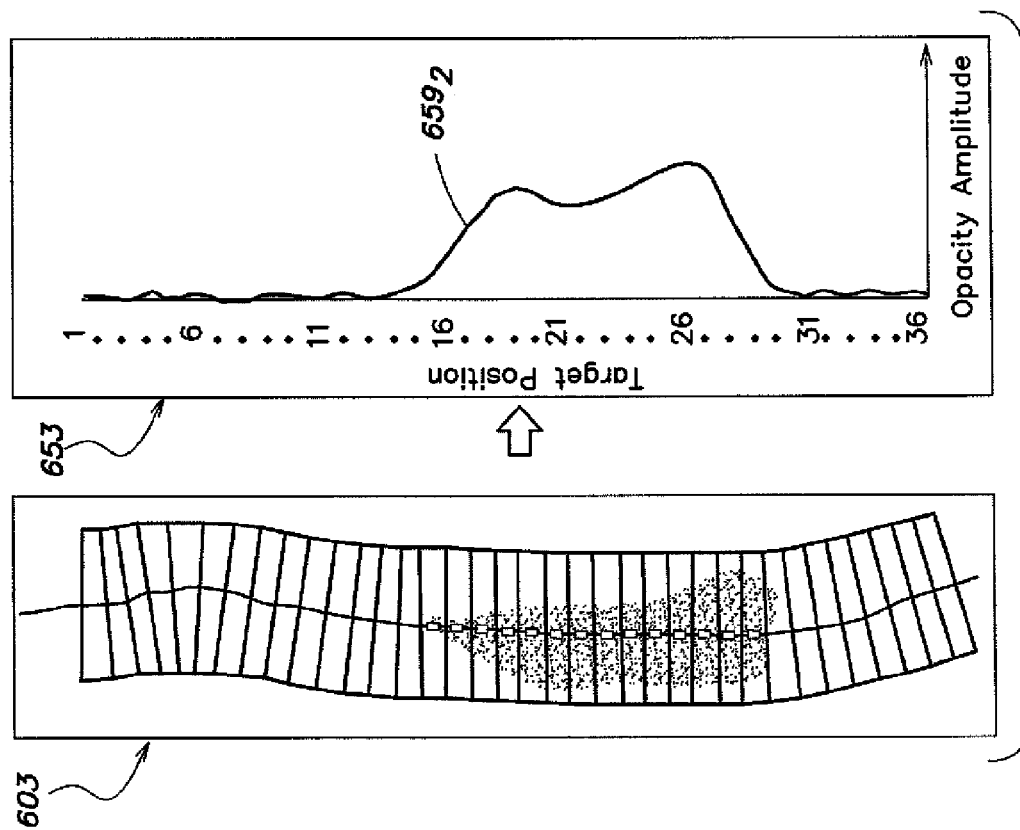
Figure 6B:
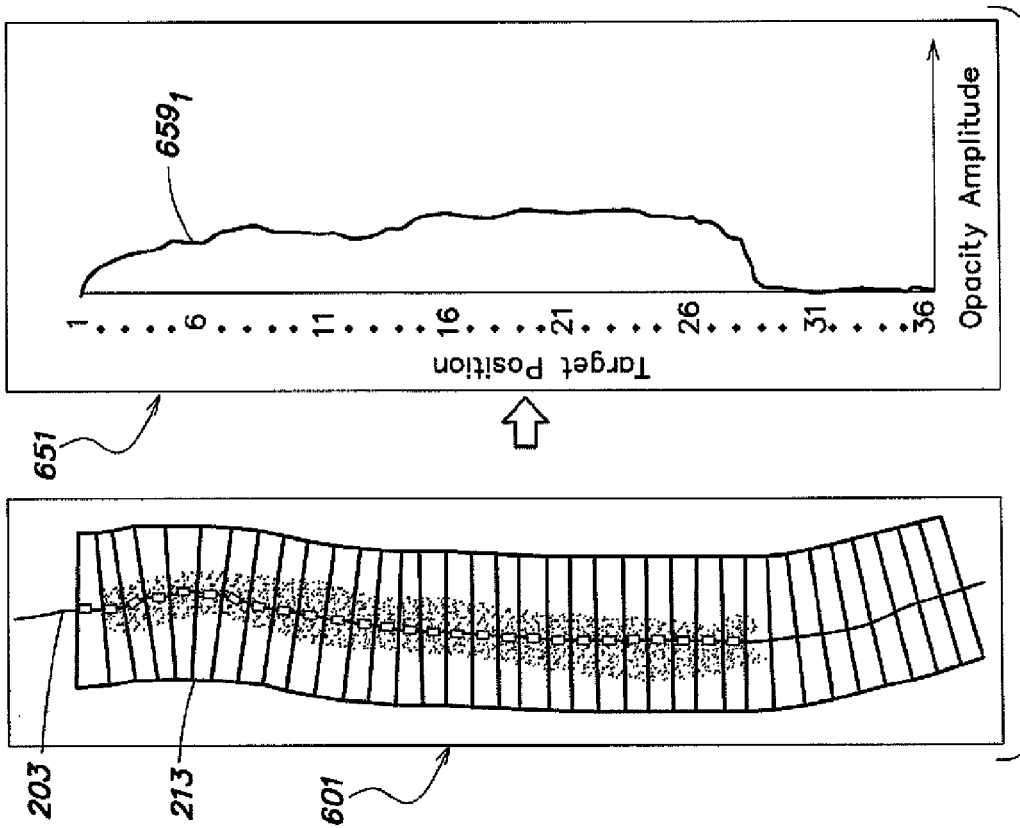
Figure 7B:
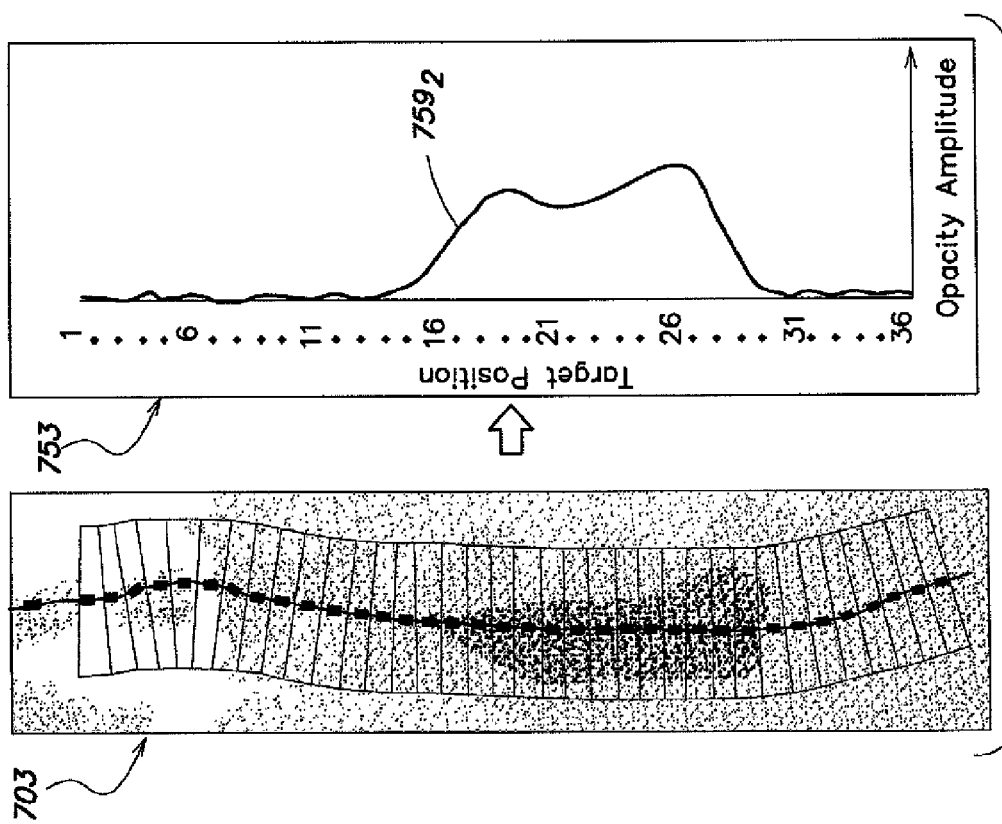
FIGS. 7A-7D illustrates a series of 4 radiographic images and corresponding profiles when the corresponding baseline field intensity is subtracted from each of the field intensities for each image of a series of images.
Figure 7A:
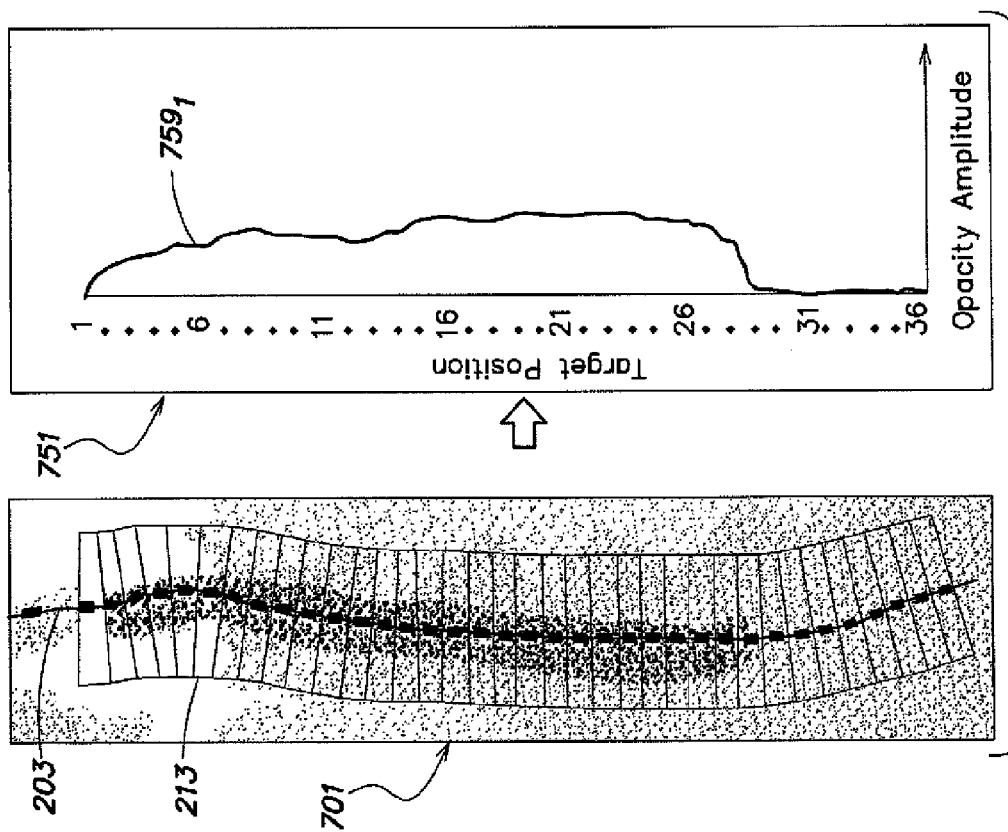
Figure 7D:
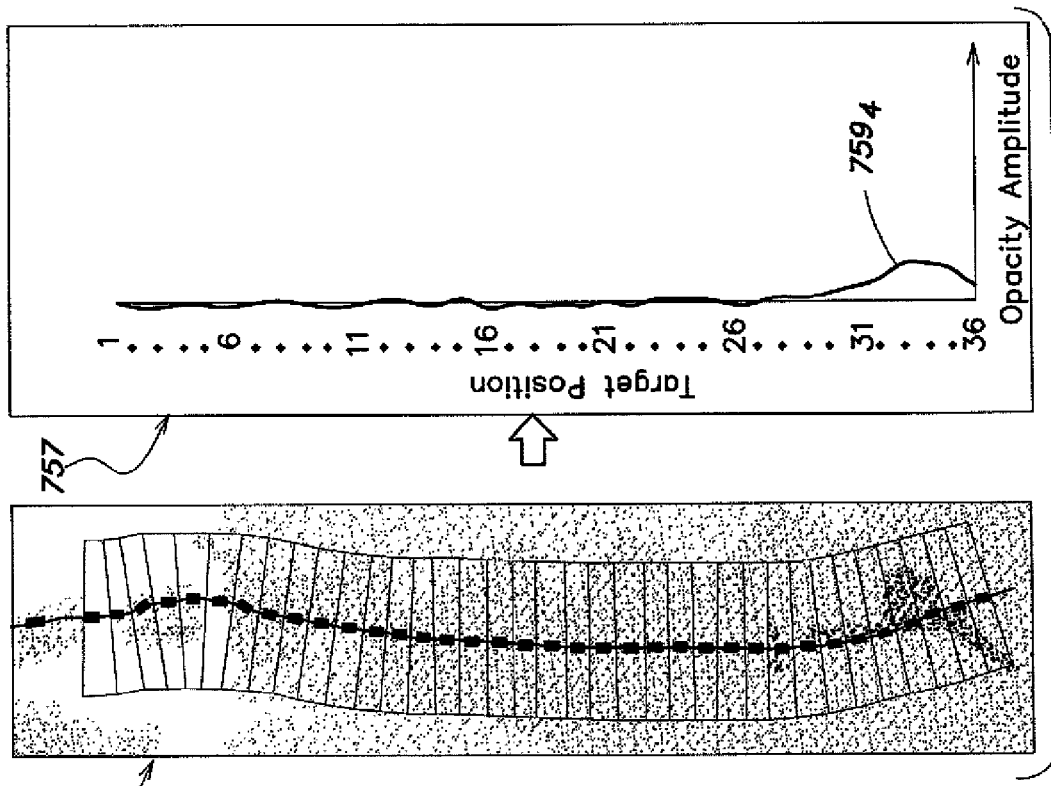
Figure 7C:
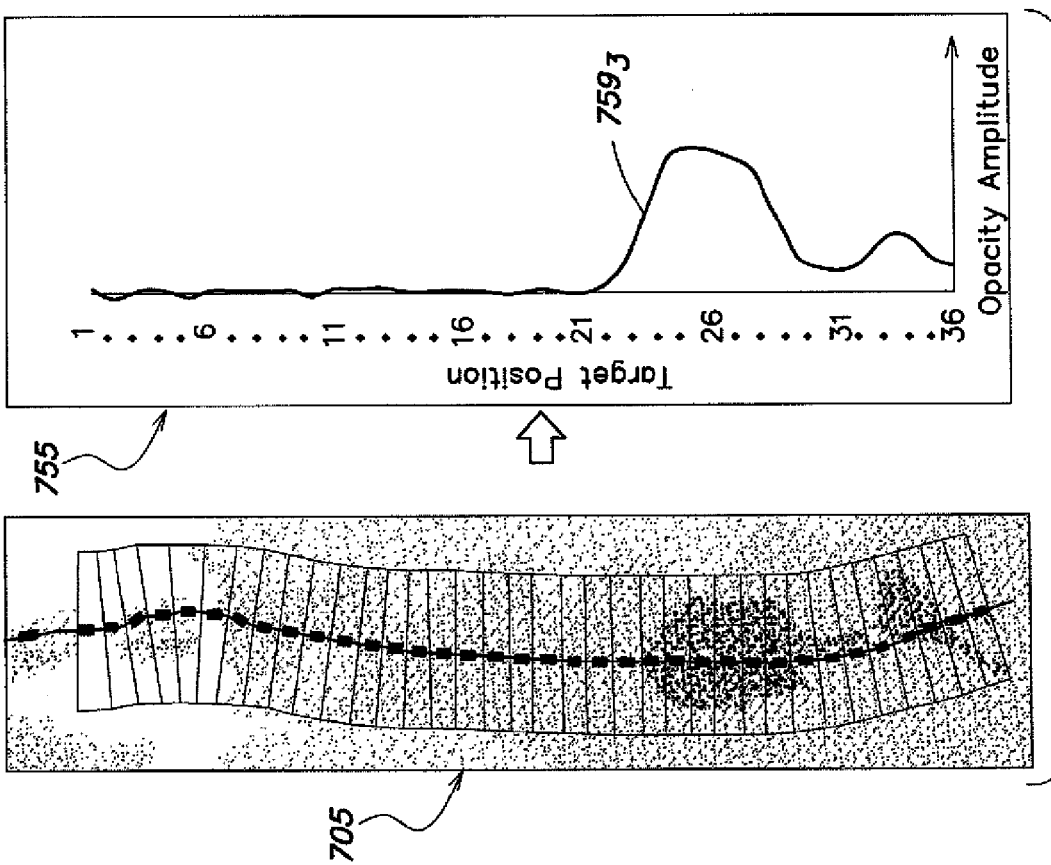

In the second example embodiment of step 113, local image fields are defined for the baseline radiographic image in the same way described in step 111, which can be done at any suitable time, such as during the study, post hoc, or both. Baseline field intensities are then determined for each field of the baseline image in the same way described in step 115. The baseline field intensities are subtracted from the corresponding field intensities in each of the series of radiographic images. FIG. 5C illustrates a resulting intensity profile for an image formed with no contrast material. In this example, local image fields are formed in the ladder structure as described above. In plot 510 the baseline field intensity in the local image fields are represented as opacity of the objects in the image. As shown, opacity is plotted as a function of the position along the curve defined at step 109.

As illustrated by FIG. 5C, the opacity profile in plot 510 is subtracted from the field intensity profile determined for each image in step 115. This correction reduces the bias in each field's subsequent intensity that results from variations in the baseline image intensity. Plot 520, illustrates that in the ideal case, when the baseline is subtracted from intensity values associated with the local image fields of an image containing no contrast material, the opacity profile is zero along the curve.

In yet a further approach to the processing at block 113, a baseline may be determined for an entire image. The baseline may then be subtracted from subsequent frames as they are collected.

FIGS. 6A-6D illustrate a series of sequential radiographic images 601, 603, 605, and 607, or frames, of a barium swallow passing through a patient's esophagus. These images have been corrected to cancel the baseline image contribution according to the first example embodiment of step 113. In each of the images, the bolus appears as a darkish blob, and within the blob are noticeable spots at the radiopaque target locations. The bolus clearly appears to advance downwards over the sequence of images. Notice also that a ladder local image field structure is superimposed for illustrative purposes.

In FIGS. 6A-6D, line plots 651, 653, 655, and 657, respectively, provide a quantitative indication of the bolus location by determining the opacity within each local image field. In this example, the ladder structure 213 has been used to define the local image fields at successive intervals in time as a bolus of contrast material moves through a lumen. The profiles $659_1, \ldots, 659_4$ illustrate quantitatively the progression of the bolus down the patient's esophagus.

As shown, plots 651, 653, 655 and 657 are 2-D plots, each indicating quantity as a function of position. Here position is measured along the curve defined at step 109. The distance along the curve in this example is determined based on the equally spaced targets that were used to define local image fields. In the example of FIGS. 6A-6D in which the curve is not straight, the position along the curve may not correlate directly to locations in the image. It may be desirable when analyzing data to view data displayed positionally relative to the curve rather than image coordinates because the curve follows the bodily lumen. In this way, the data may more intuitively represent movement though the bodily lumen. Therefore the plot may provide a depiction of measured data that facilitates understand of the functioning of the bodily lumen.

In embodiments in which the contrast material is fully opaque or substantially fully opaque, the quantitative indication of the amount of contrast material may be an indication of the cross-sectional width of the bolus at each target location. In embodiments in which the bolus is substantially circular in the transverse plane, such a quantitative indication may serve as an indication of volume. Though, it is not a requirement of the invention that the quantitative indication be a volume or otherwise have any specific dimensions.

FIGS. 7A-7D provides analysis of the same dataset using the second example embodiment of step 113. The background structure, observed initially in the baseline image 201 (FIG. 5C) is recognizable in each of the radiographic images 701, 703, 705, and 707. The intensity in the local image fields is determined in each radiographic image and then the baseline intensity, plotted in subfigure 510 of FIG. 5C, is subtracted from the respective field intensity for each image. The results are plotted in plots 751, 753, 755, and 757. In comparing the profile data $759_1, \ldots, 759_4$ of FIGS. 7A-7D to the respective profile data $659_1, \ldots, 659_4$ in FIGS. 6A-6D, it is clear that in this example, the results are quite similar using either approach for adjusting for baseline image intensity.

Returning to FIG. 1, the process continues in step 117, where the collected data is displayed. As should be apparent to one of skill in the art from the attached figures, the display may be rendered by a computer on a display device, though any suitable device may be used. The profile data may be displayed in any suitable way. For example, the profile data may simply be plotted as a series of line plots as was done in FIGS. 6A-6D and FIGS. 7A-7D. Alternatively, the line plots may be superimposed onto a single axis and distinguished using, for example, different colors, patterns, markers, or any suitable combination thereof. In some embodiments, the line plots are displayed in succession, registered to a common coordinate system so as to appear as an animation or video to a viewer.

In another embodiment, data collected from a series of frames may be collectively displayed on a spatiotemporal plot having a time axis and a spatial axis. The time axis may represent the relative time of acquisition of each radiographic image. The spatial axis represents the position along the curve with which the field intensity data is associated. The field intensity may be represented using color, contour lines, density patterns, or any other suitable representation. In this way a viewer may observe registered data determined from multiple radiographic images simultaneously on a single plot.

In some embodiments, the data representing the specified distribution of the contrast material is combined and co-registered for display with other high-resolution physiological data, such as pressure. The relationship between the contrast material position and distribution of the other physiological property can be readily identified and may provide new insight into the physiology and pathophysiology of the organ in general and individual clinical cases in particular.

Figure 8:
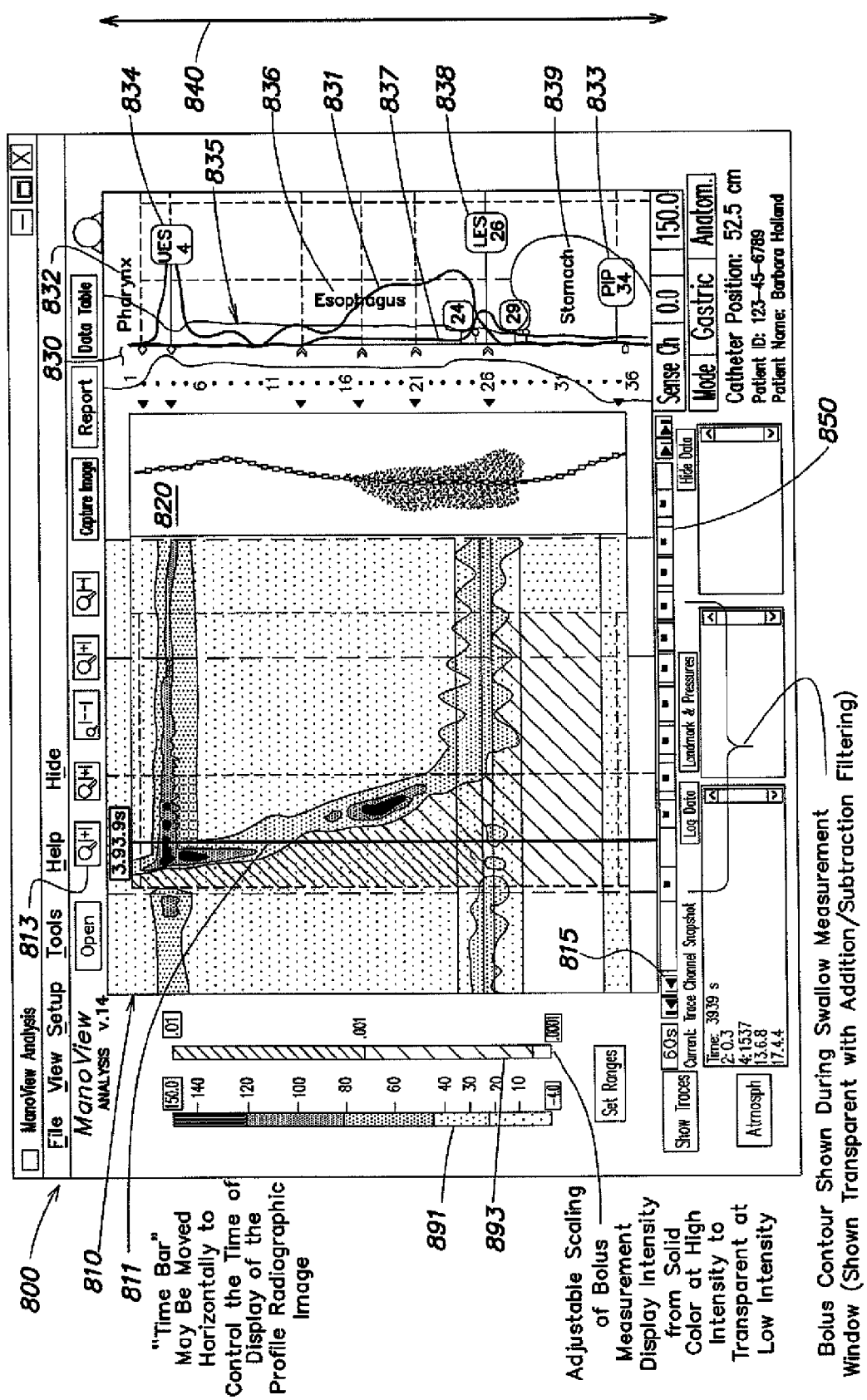
FIG. 8 is an illustration of a user interface for displaying positional information of a bolus co-registered with pressure data on a spatiotemporal plot and a profile plot according to an embodiment of the invention.

An example of such co-registration of data is shown in FIG. 8. In this embodiment, the data is displayed in a user interface that allows a user to manipulate the appearance and presentation of the data. An example is shown in FIG. 8 which illustrates an embodiment using the ManoView™ software user interface 800 developed for display and analysis of pressure data along a bodily lumen. In the illustrated user interface 800, the profile data indicates the location of a bolus in a patient's upper GI tract in combination with pressure data, which may serve as an indication of muscle contractions in the GI tract.

The user interface may display the profile data in any suitable way. In some embodiments, the display may include multiple different representations of the data simultaneously. In the example of user interface 800, a contour display region 810 and a profile display region 830 are displayed in combination with a radiographic image 820.

The contour display region 810 provides a spatiotemporal plot of the bolus position and pressure data. The spatial axis 840 extends vertically and the time axis 850 extends horizontally. The interface may allow a user to manipulate the displayed data with any suitable zoom controller 813, scroll bar 815, or similar display control that may be used to select which portion of the swallow sequence is displayed in embodiments in which the data is displayed after a study is completed.

Profile display region 830 shows the data at an instant of time. For post-hoe display, that instant of time may be selected by the position of time control 811. For real time data display, the profile plot may display data as it is collected.

In some embodiments, the bolus positional data displayed in the contour display region 810 may be superimposed with other data spatially and temporally co-registered with the axes. In the present example, pressure data is data is presented with the positional data in the contour display region 810. The positional or pressure data may have a variable transparency. Also, the positional and pressure data may be displayed using different color scales to enable both datasets to be viewed simultaneously on the same set of axes. In the embodiment illustrated in FIG. 8, a display scale 891 is provided to indicate the color and/or transparency used to represent pressure data. A second display scale 893 is provided to indicate the color and/or transparency used to represent bolus positional data. In the embodiment illustrated, a continuum of colors and/or transparencies are each type of data.

By co-registering the bolus positional data with pressure data along the spatial axis the interaction of pressure and bolus position may be precisely and intuitively visualized. In embodiments in which pressure sensors on a catheter also serve as radiopaque targets, the pressure measurements may be readily correlated positionally to measurement of the quantity of bolus in the vicinity of the targets. Though, other registration approaches are possibly.

Such a display may facilitate review of data. With pressure measurement alone, it is not always possible to determine where the bolus is and whether it has cleared properly during a swallow sequence. With radiographic profile data alone the movement of the bolus is seen, but it is not always possible to identify the degree to which movement or lack thereof is the result of motor function within the organ (such as peristaltic contraction and appropriate contraction or relaxation of sphincter muscles) or of other effects such as gravity or structural effects. By co-registering these data in position, both the movement of the bolus and the physiological pressure ("motor function") that drives it are clearly displayed, allowing the reviewer to quickly identify the source of bolus movement anomalies and conversely identify the functional affect of physiological anomalies on bolus flow. Methods and systems for displaying multiple properties are described in U.S. patent application Ser. No. 12/148,679, entitled "Diagnostic System for Display of High-Resolution Physiological Data of Multiple Properties," and U.S. patent application Ser. No. 10/281,068, entitled "Visualization of Values of a Physical Property Detected in an Organism Over Time,"_ each of which are hereby incorporated by reference in their entireties.

Other types of data may be presented along with the contour plot. The profile display region 830 in the example user interface 800 provides a line plot 831 of the bolus profile. Also shown is a pressure profile 837 which may be measured using sensors correlated positionally to the radiopaque targets. The contour plot and the profile plots may be displayed so that the position axis 840 of the profile display region 830 may be registered with the position axis of contour display region 810. The profile display region 830 may be configured to display the bolus profile 831 at the time on the time axis 850 indicated by the time bar 811. The user interface 800 also may be configured to display a radiographic image 820 from which the bolus profile 831 is determined. The radiographic image may be displayed after subtraction of the baseline image; without baseline correction; with or without the local image fields, target locations, or curve superimposed; or in any other suitable way.

In some embodiments, an illustration of anatomy of the region where measurements were taken may be shown along with the data. In the example shown in user interface 800, the measurement data is collected along the upper gastrointestinal (GI) tract. A reference rendering 835 of the anatomy of that region of the body is shown as part of the profile display region 830.

The reference rendering 835 may have a number of reference features to clearly illustrate the position of the measurement data relative to important features of the surrounding area. In the example where reference rendering 835 is the upper GI tract, the reference features may include the pharynx 832, upper esophageal sphincter (UES), esophagus 836, lower esophageal sphincter (LES), stomach 839, and the like.

As illustrated in FIG. 8, a user interface 800 presenting an illustration of anatomy may have one or more landmarks, such as landmarks 834 and 838 corresponding to the UES and LES respectively. The landmarks may act as control features, allowing a user or computer processing to specify the location of the certain portions of the anatomy relative to the axis 840 based on displayed pressure data. A user, for example, could position these landmarks based portions of the pressure data showing relatively high pressure associated with sphincter activity. By correlating the illustration to the specified location of the landmarks, the computer may adjust the illustration of the anatomy by scaling and positioning it relative to spatial axis 840 for the specific situation, e.g., patients of different sizes.

While method 100 has been described with the example of a radiographic imaging system using radiopaque targets and a suitable contrast material, other suitable imaging systems known in the art may be used. For example, in some embodiments, an ultrasonic imaging system may be used. In such an embodiment, suitable targets and contrast material may be of sufficient density to appear with high contrast in the ultrasonic image. As another example, radionuclide imaging techniques known from nuclear medicine may be used.

Figure 11A:
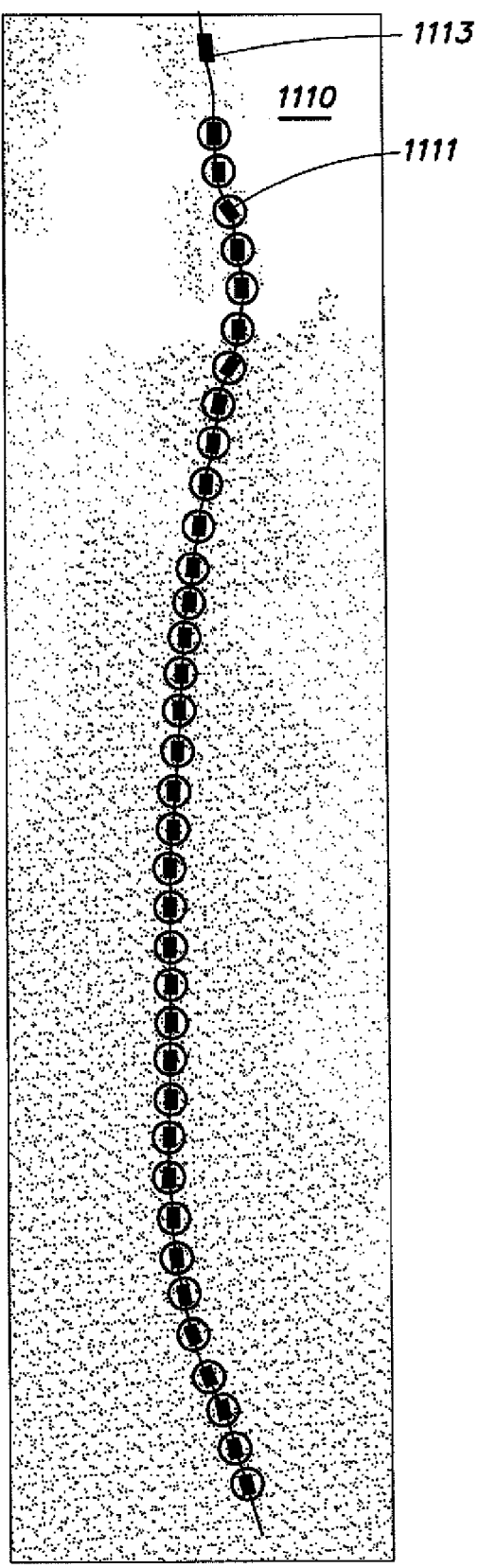
FIG. 11 is a set of radiographic images illustrating the movement of radiopaque targets during a diagnostic procedure.
Figure 11B:
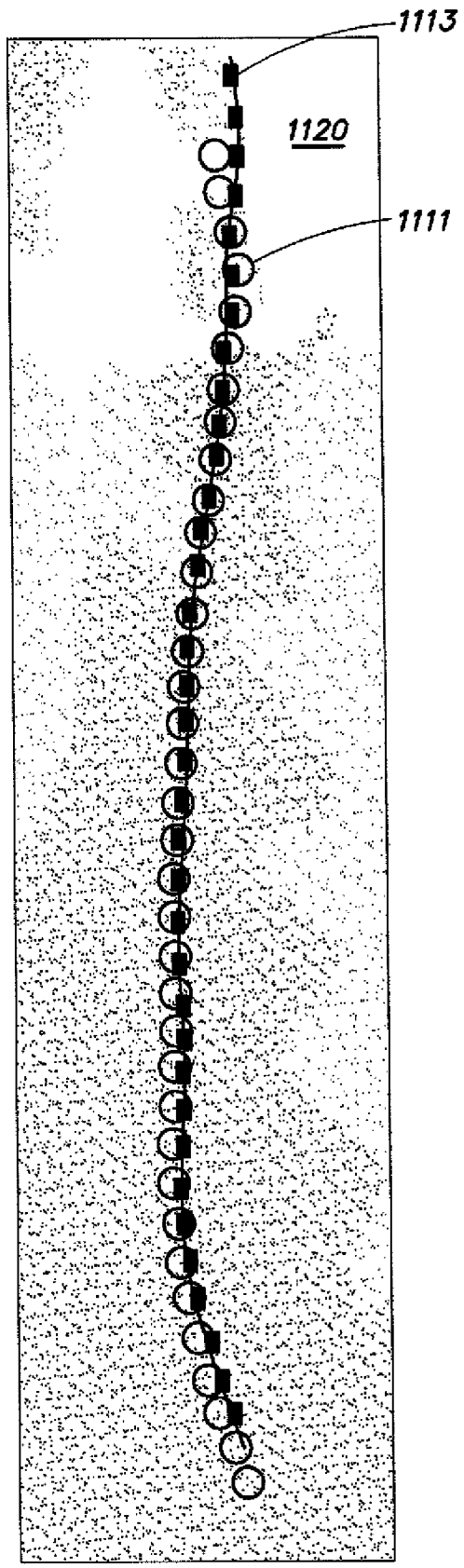

In some embodiments of method 100 the catheter may move during the course of a radiographic study. FIG. 11 shows an example of the catheter moving during the course of the radiographic study. The target locations 111 initially identified from radiographic image 1110 are no longer accurate with respect to radiographic image 1120. To adjust for movement, the movement may be tracked and the target locations relative to the image frames may be adjusted dynamically. Tracking such movement and repositioning the local fields dynamically may be complicated by the fact that the radiopaque contrast media may obscure the targets at some times. Processing images based on target locations when some targets are not observable may be achieved in several ways. For example, targets that remain visible during passage of the contrast material may be tracked and the position of the obscured targets and fields estimated by interpolation or extrapolation. Alternatively, the targets may be re-identified after passage of the material (e.g., between swallows in a barium swallow study) and the location and orientation of the resulting local image fields established. The local image fields may then be made mobile by interpolating their positions and orientations in time between their initial positions and orientations and their re-established positions and orientations.

Figure 10:
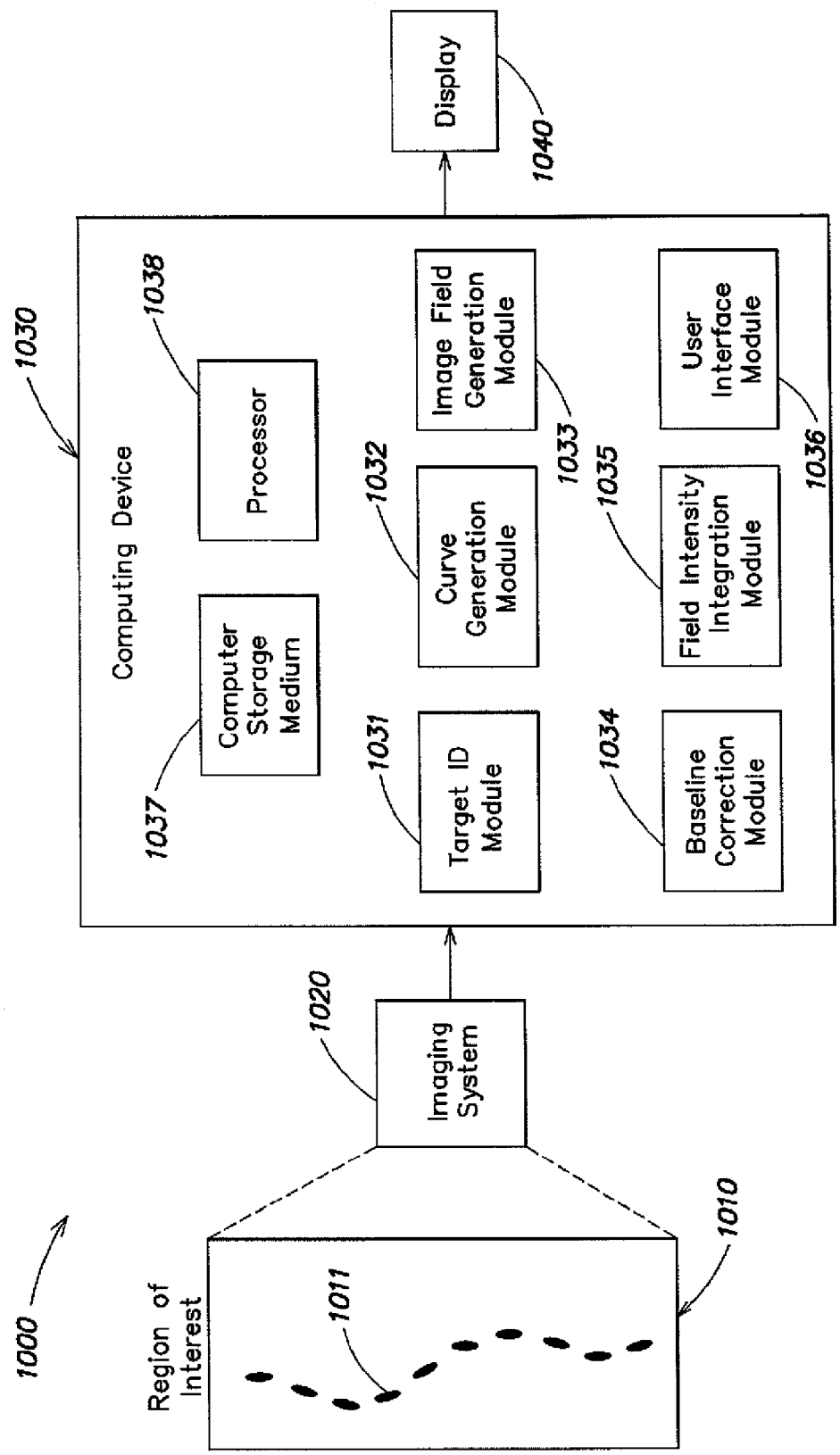
FIG. 10 is a system for collecting diagnostic data according to some embodiments of the invention.

The method 100 may be implemented using any suitable system. FIG. 10 illustrates a system 1000 according to some embodiments. The system 1000 has one or more targets 1011 positioned in a region of interest 1010, an imaging system 1020, a computing device 1030, and a display 1040. A commercially available medical imaging system may be used, but any imaging system 1020 suitable for imaging the region of interest 1010 may be used. The targets 1011 are of suitable size, shape, and material composition so as to be detected by imaging system 1020 and identifiable as targets once imaged.

The imaging system 1020 may image the region of interest prior to the introduction of a contrast material to establish a baseline image. Once a suitable contrast material is introduced into the region of interest 1010, the imaging system may be configured to acquire a series of images.

The computing device 1030, may be of a type known in the art for processing medical image data, and may be operably connected to the imaging system 1020 to receive the series of images in real time or any subsequent time. The computing device 1030 may be configured to perform steps of method 100 using computer-executable modules stored in a computer storage medium 1037 of the device and executed by a suitable processor 1038. For example, the computing device may have a target identification module 1031 for identifying target locations in each image. Optionally a user interface module 1036 may be provided for a user to manually designate target positions.

A curve generation module 1032 may be used to generate a suitable curve. An image field generation module 1033 may be used to generate the local image fields using the curve and/or target location information. A baseline correction module 1034 may optionally be used to cancel the contribution of the baseline image. A field intensity integration module 1035 may be used to determine the field intensity in local image fields.

A user interface module 1036 may be configured to output the data for display on display 1040. Any suitable display technique may be used.

It should be appreciated that some embodiments enable a physician to rapidly and quantitatively assess transit of the contrast material through a bodily lumen. In the example of user interface 800 (FIG. 8), where a barium swallow study is shown, the physician can simply scroll through temporal plots of the resulting data (e.g. a temporally continuous contour plot) and obtain a complete representation of the bolus movement without needing to take the time to watch each swallow as a video. A physician may be able to observe and diagnose abnormalities indicative of esophageal diseases such as achalasia, dysphagia, diffuse esophageal spasm, ineffective esophageal motility, and hypertensive LES. For example, a physician may reliably identify lumenal obstructions (e.g., structural effects such as strictures) via persistent low bolus signal throughout a swallow sequence.

It should be appreciated that scrolling through bolus position information is just one example of a mechanism by which the information can be reviewed. As depicted, the quantitative positional information can be displayed on a contour plot, which allows a quantitative history of bolus position during a swallow study or other procedure to be viewed in a single image. In contrast, conventional approaches required the reviewer to watch a video of the swallow and combine in his imagination the salient features of the swallow to make a determination of normalcy or pathology.

It should be appreciated that when bolus position data is combined and co-registered with other high-resolution physiological data, such as pressure, the relationship between the material position and distribution of the other physiological property can be readily identified and provide new insight into the physiology and pathophysiology of the organ in general and individual clinical cases in particular.

The quantitative information allows, in certain pathologies, landmarks (e.g. UES and LES) to be more easily identified in one modality (e.g. pressure or fluoroscopy or other radiographic image) versus the other. By combining multiple types of data in one image, the landmarks may be identified in whichever modality is most suitable and that information can help interpret the results of the modality in which the landmark may not be reliably identified.

It should be appreciated that bolus position data obtained according to method 100 provides a reliable, quantitative indication of, for example, bolus movement. Heretofore, bolus measurement methods only provided qualitative measurement of bolus movement leaving ambiguity in the determination of swallow performance. For example, ambiguity exists in multi-channel intraluminal impedance measurements as to whether sufficient bolus has cleared the lumen, whether the bolus substantially remains in the lumen, or whether meaningful "bolus escape" (i.e., retrograde flow) has occurred.

Having thus described several aspects of at least one embodiment of this invention, it is to be appreciated that various alterations, modifications, and improvements will readily occur to those skilled in the art. For example, display information may be registered and combined.

Aspects described above may be used separately and the inventor believes they remain unique. For example, intensity measurements obtained from changes in the local image fields may be displayed using techniques other than profile or spatiotemporal contour plots. Similarly the local image fields may be specified post hoc and the changes measured over time therein used to generate a spatiotemporal data set describing the contrasted media movement over time.

The method may be applied to other areas than the esophagus and outside the GI tract in general. For example it may be employed in the urinary tract, vascular network, and other visceral systems in which mobile material may be imaged and a target device may be introduced.

Further, embodiments are described in which quantitative information about position of contrast material is derived by constructing fields based on locations of targets in a radiographic image. Other approaches for constructing fields are possible, including using the image of the contrast material to define the fields. For example, a barium swallow fluoroscopic study could be reviewed and landmarks along the lumen identified, either manually by a reviewer or using computer analysis, via their radiographic signatures (e.g. constriction of the barium bolus image at a sphincter). A line or curve could then be constructed along the axis of the lumen image by identifying the path of the contrast material as it transits through the lumen. Multiple local image fields constructed along this line or curve. Once lical fields are constructed, the change in intensity in those local fields can be measured as it is in the case where radiopaque markers are introduced.

Such alterations, modifications, and improvements are intended to be part of this disclosure, and are intended to be within the spirit and scope of the invention. Accordingly, the foregoing description and drawings are by way of example only. The above-described embodiments of the present invention can be implemented in any of numerous ways. For example, the embodiments may be implemented using hardware, software or a combination thereof to obtain and produce the displays of physiological data. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "Program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of collecting diagnostic data, the method comprising:
   capturing a series of frames at each of a plurality of successive times, the frames comprising radiographic imaging data of a bodily lumen of a patient as a radiographic contrast material transits through the lumen;
   processing the series of frames to compute:
   a plurality of fields, each field being representative of a region along the lumen, and for each frame, a quantitative indication of an amount of the contrast material in a plurality of regions, each region being associated with a respective field of the plurality of fields; and providing as an output a quantitative indication of the amount of the contrast material at each of a plurality of locations along the bodily lumen as a function of time based on the computed quantitative indications.

2. The method of claim 1, wherein:

a member comprising a plurality of radiopaque targets is within a bodily lumen of a patient, the plurality of radiopaque targets having predefined positions with respect to each other;

the computing the plurality of fields comprises identifying the plurality of fields based on a representation of the plurality of radiopaque targets in the plurality of frames; and the processing the series of frames comprises computing an intensity of the radiographic imaging data in each of a plurality fields, each of the plurality of fields being adjacent a radiopaque target of the plurality of radiopaque targets.

3. The method of claim 2, wherein:

computing the quantitative indication of the amount comprises weighting the computed intensity in each of the plurality of fields by the size of the field.

4. The method of claim 2, further comprising determining a baseline by:

acquiring a baseline image of the bodily lumen with the member in the lumen and without the contrast material in the lumen; and computing from the baseline image a baseline intensity in each of the plurality of fields.

5. The method of claim 4, wherein:

computing the quantitative indication of amount of the contrast material in the plurality of regions comprises computing a quantitative indication of amount in each of the plurality of fields; and processing the series of frames comprises, prior to computing the quantitative indication of amount, offsetting measured values in each frame based on the baseline.

6. The method of claim 1, wherein providing an output comprises providing an output indicating the amount of the contrast material at each of a plurality of locations in a linear coordinate system representing distance along the lumen, the linear coordinate system being independent of a coordinate system of the image.

7. The method of claim 1, wherein:

a member comprising a plurality of radiopaque targets is within a bodily lumen of a patient, the plurality of radiopaque targets having predefined positions with respect to each other;

the computing the plurality of fields comprises identifying the plurality of fields based on a representation of the plurality of radiopaque targets in the plurality of frames.

8. The method of claim 7 wherein processing the series of frames comprises, for each frame:

identifying representations of the plurality of radiopaque targets;

constructing a curve that connects the representations of the plurality of radiopaque targets in the frame;

constructing a plurality of fields in the frame, each field being associated with a segment along the curve in the vicinity of a representation of a target of the plurality of radiopaque targets; and computing a quantitative indication of the amount of the contrast material at each of the plurality of locations based on an intensity indicated by radiographic imaging data associated with the field.

9. The method of claim 1, wherein the bodily lumen comprises a portion of a gastrointestinal tract of the patient and the contrast material comprises a barium swallow.

10. The method of claim 8, wherein:

the member comprises a pressure sensing catheter;

the pressure sensing catheter comprises a plurality of pressure sensors, each positionally associated with a radiopaque target of the plurality of radiopaque targets; and the method further comprises:

while capturing the series of frames, capturing pressure data based on outputs of the plurality of pressure sensors; and displaying a spatiotemporal plot having a position axis and a time axis, the position axis representing a position along the lumen, the plot representing the quantitative indication of the amount of the contrast material and the pressure data co-registered in position and time.

11. The method of claim 10, wherein:

the method further comprises displaying on a second plot adjacent to the spatiotemporal plot and registered with the position axis, for a select time, the quantitative indication of the amount of the contrast material and the pressure data for the select time; and wherein the displaying the spatiotemporal plot occurs post hoc.

12. The method of claim 10, further comprising:

displaying, in conjunction with the spatiotemporal plot, a depiction of the bodily lumen with anatomical landmarks registered with the position axis.

13. The method of claim 1, wherein computing a plurality of fields, comprises:

identifying a plurality of landmarks along the lumen based on a signature within the series of frames;

constructing a curve along the lumen based on the location of the landmarks; and constructing fields along the curve.

14. A system for collecting diagnostic data, the system comprising:

a computing device configured to receive a plurality of radiographic images from a radiographic imaging system, each of the plurality of images representing a region containing a plurality of radiopaque targets and a contrast material, each radiopaque target associated with a location in the radiographic image, and configured to compute a plurality of values from each radiographic image, each value being computed from at least an intensity of the radiographic image in a local image field to provide a quantitative indication of an amount of the contrast material within the local image field, each local image field being associated with a portion along a path in a radiographic image of the plurality of radiographic images, the path being based on at least the locations of the plurality of radiopaque targets within the radiographic image; and a display device configured to display the plurality of values as a function of the position along the path for each of the plurality of radiographic images.

15. The system of claim 14, wherein:

the radiographic imaging system is further configured to acquire a baseline image, the baseline image representing the region at a time at which the contrast material is absent; and the computing device is further configured to subtract the baseline image from the radiographic image.

16. The system of claim 15, wherein the computing device subtracts the baseline image from a radiographic image among the plurality of radiographic images before computing the plurality of values for said radiographic image.

17. The system of claim 15, wherein:
the computing device is further configured to calculate a plurality of baseline values, each baseline value being an intensity of the baseline image in the local image field for a respective position along the path; and
for a radiographic image among the plurality of radiographic images, each value from the plurality of values is computed by subtracting a respective baseline value from the plurality of baseline values from the intensity of the radiographic image in the local image field for the respective position along the path.

18. The system of claim 14, wherein:
the plurality of radiographic images are received successively;
the computing device is configured to compute the plurality of values for each radiographic image among the plurality of radiographic images in real time; and
the display is further configured to display the plurality of values in real time.

19. The system of claim 14, wherein the display is further configured to display for each radiographic image among the plurality of radiographic images, the corresponding plurality of values on a spatiotemporal plot, the spatiotemporal plot comprising a position axis and a time axis, wherein for each radiographic image each of the values of the corresponding plurality of values are plotted at the corresponding position along the path on the position axis and at a time on the time axis corresponding to a time at which the image was acquired.

20. The system of claim 14, wherein the computing device is further configured to determine the location of each radiopaque target from a radiographic image among the plurality of radiographic images.

21. The system of claim 14, wherein the plurality of radiopaque targets are attached to a catheter adapted for insertion in a bodily lumen.

22. The system of claim 21, wherein the catheter further comprises pressure sensors.

23. The system of claim 22, wherein the display is further configured to display pressure data measured with the pressure sensors.

24. The system of claim 14, further comprising:
a catheter comprising a plurality of pressure sensors incorporated along a length of said catheter,
wherein, each of the plurality of pressure sensors has a position along the path,
wherein, each of the plurality of pressure sensors obtain pressure data, and
wherein, the display displays the pressure data co-registered with the display of the plurality of values.

25. A system comprising:
a computing device configured to receive an image from an imaging system, the image representing a region containing a target and a contrast material, and configured to compute a plurality of values, each value being associated with a respective local image field of a plurality of local image fields in the image, each value being computed from at least an intensity of the image in the respective local image field for a position along a path to provide a quantitative indication of an amount of the contrast material at the position, the path being based on at least a location of the target in the image; and
a display device configured to display the plurality of values as a function of the position along the path.

26. The system of claim 25, wherein the target is among a plurality of targets within the region, each imaged at a respective location, and the path is based on at least the respective locations of each of the plurality of targets.

27. The system of claim 25, wherein:
the computing device is further configured to receive a plurality of successive images, the image being among the plurality of successive images; and
the computing device is configured to compute a respective plurality of values from each successive radiographic image.

28. The system of claim 25, wherein the image is a radiographic image and the target is a radiopaque target.

29. The system of claim 25, wherein the image is an ultrasonic image.

30. The system of claim 25, wherein the image is a radionuclide image.

31. A computer storage medium comprising computer executable instructions that, when executed on a computer, perform a method of processing diagnostic data using frames from a radiographic imaging system, the frames comprising intensity data indicative of attenuation of radiation passing through a bodily lumen of a patient, the frames being acquired at a plurality of successive times during which a member is present in the lumen, the member comprising a plurality of radiopaque regions identifiable in the frames, and the method comprising:
for each frame:
determining within the frame a plurality of fields, each field representing a region around a corresponding radiopaque region of the plurality of radiopaque regions;
for each field of the plurality of fields within the frame:
computing, based on the intensity within the field, a value indicative of a quantity of contrast material in the frame; and
associating in computer storage media coupled to the computer the computed value indicative of the quantity with a spatial position along the lumen, the lumen being based on the position of the corresponding radiopaque region along the member.

32. The computer storage medium of claim 31, wherein the method further comprises:
presenting on a display device associated with the computer a time varying plot, the plot having a coordinate system comprising a first axis representing the spatial position along the lumen and a second axis representing the quantity of contrast material at each of a plurality of locations along the lumen.

33. The computer storage medium of claim 32, wherein the plot is a time-varying line plot.

34. The computer storage medium of claim 32, wherein the plot is a contour plot.

* * * * *